US008252756B2

(12) United States Patent
Mirkin et al.

(10) Patent No.: US 8,252,756 B2
(45) Date of Patent: Aug. 28, 2012

(54) NUCLEIC ACID FUNCTIONALIZED NANOPARTICLES FOR THERAPEUTIC APPLICATIONS

(75) Inventors: Chad A. Mirkin, Wilmette, IL (US); Nathaniel L. Rosi, Pittsburgh, PA (US); C. Shad Thaxton, Chicago, IL (US); David A. Giljohann, Chicago, IL (US)

(73) Assignee: Northwestern University, Evanston, IL (US)

( * ) Notice: Subject to any disclaimer, the term of this patent is extended or adjusted under 35 U.S.C. 154(b) by 454 days.

(21) Appl. No.: 11/917,680

(22) PCT Filed: Jun. 8, 2006

(86) PCT No.: PCT/US2006/022325
§ 371 (c)(1),
(2), (4) Date: Apr. 3, 2009

(87) PCT Pub. No.: WO2006/138145
PCT Pub. Date: Dec. 28, 2006

(65) Prior Publication Data
US 2009/0209629 A1    Aug. 20, 2009

Related U.S. Application Data

(60) Provisional application No. 60/690,379, filed on Jun. 14, 2005, provisional application No. 60/739,556, filed on Nov. 23, 2005, provisional application No. 60/709,022, filed on Aug. 17, 2005, provisional application No. 60/801,124, filed on May 17, 2006.

(51) Int. Cl.
*A61K 48/00* (2006.01)
(52) U.S. Cl. ...... 514/44; 536/24.5; 536/24.31; 536/24.1
(58) Field of Classification Search .................. None
See application file for complete search history.

(56) References Cited

U.S. PATENT DOCUMENTS

| | | | |
|---|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |

(Continued)

FOREIGN PATENT DOCUMENTS
EP    1072679    1/2001
(Continued)

OTHER PUBLICATIONS

Hussain et al. Journal of Controlled Release, 2004, vol. 99: 139-155).*
Sandhu et al. Bioconjugate Chem 2002, 13: 3-6.*
Jeong et al. Bioconjugate Chemistry 2003, 14: 473-479.*
Ahmadi et al., Shape-Controlled Synthesis of Colloidal Platinum Nanoparticles. Science. Jun. 28, 1996;272(5270):1924-6.
Allara and Tompkins, J. Colloid Interface Sci., 49, 410-421 (1974).
Allara et al., Spontaneously organized molecular assemblies. 1. Formation, dynamics, and physical properties of n-alkanoic acids adsorbed from solution on an oxidized aluminum surface. Langmuir 1985; 1(1): 45-52.
Bahnemann, in Photochemical Conversion and Storage of Solar Energy (eds. Pelizetti and Schiavello 1991), 251-276.
Bharali et al., Organically modified silica nanoparticles: a nonviral vector for in vivo gene delivery and expression in the brain. Proc Natl Acad Sci U S A. Aug. 9, 2005;102(32):11539-44.

(Continued)

*Primary Examiner* — Kimberly Chong
(74) *Attorney, Agent, or Firm* — Marshall, Gerstein & Borun LLP

(57) ABSTRACT

Materials and methods for regulating gene expression using nanoparticles functionalized with antisense oligonucleotides are provided.

42 Claims, 14 Drawing Sheets

U.S. PATENT DOCUMENTS

| | | | |
|---|---|---|---|
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler et al. |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,506,564 B1 | 1/2003 | Mirkin et al. |
| 6,656,730 B1 | 12/2003 | Manoharan |
| 6,750,016 B2 | 6/2004 | Mirkin et al. |
| 6,767,702 B2 | 7/2004 | Mirkin et al. |
| 7,238,472 B2 | 7/2007 | Mirkin et al. |
| 2002/0172953 A1 | 11/2002 | Mirkin et al. |
| 2003/0147966 A1* | 8/2003 | Franzen et al. ............ 424/491 |
| 2004/0219565 A1 | 11/2004 | Kauppinen et al. |
| 2005/0059016 A1 | 3/2005 | Ecker et al. |
| 2005/0096263 A1* | 5/2005 | Keay et al. ............... 514/8 |
| 2005/0197315 A1 | 9/2005 | Taira et al. |
| 2005/0214782 A1 | 9/2005 | Chen et al. |
| 2006/0008907 A1 | 1/2006 | Friedman et al. |
| 2006/0019917 A1 | 1/2006 | Guerciolini et al. |

FOREIGN PATENT DOCUMENTS

| | | |
|---|---|---|
| WO | WO-89/02439 | 3/1989 |
| WO | WO-93/07883 | 4/1993 |
| WO | WO-93/21259 | 10/1993 |
| WO | WO-95/06731 | 3/1995 |
| WO | WO-95/11910 | 5/1995 |
| WO | WO-97/12896 | 4/1997 |
| WO | WO-98/04740 | 2/1998 |
| WO | WO-01/00876 | 1/2001 |
| WO | WO-01/51665 | 7/2001 |
| WO | WO-01/73123 | 10/2001 |
| WO | WO-02/096262 | 12/2002 |

OTHER PUBLICATIONS

Bielinska et al., DNA complexing with polyamidoamine dendrimers: implications for transfection. Bioconjug Chem. Sep.-Oct. 1999;10(5):843-50.

Brus, Quantum crystallites and nonlinear optics. Appl. Phys. A. 1991; 53(6): 465-474.
Burwell et al., Chemical Technology, 4, 370-377 (1974).
Cload et al., Polyether tethered oligonucleotide probes. J. Am. Chem. Soc. 1991; 113(16): 6324-6326.
Cook, Medicinal chemistry of antisense oligonucleotides—future opportunities. Anticancer Drug Des. Dec. 1991;6(6):585-607.
Curtis et al., A Morphology-Selective Copper Organosol. Angewandte Chemie International Edition in English Nov. 1988; 27(11): 1530-1533.
Daniel et al., Gold nanoparticles: assembly, supramolecular chemistry, quantum-size-related properties, and applications toward biology, catalysis, and nanotechnology. Chem Rev. Jan. 2004;104(1):293-346.
De Mesmaeker et al., Antisense Oligonucleotides. Acc. Chem. Res. 1995; 28(9): 366-374.
De Mesmaeker et al., Backbone modifications in oligonucleotides and peptide nucleic acid systems. Curr Opin Struct Biol. Jun. 1995;5(3):343-55.
Durand et al., Circular dichroism studies of an oligodeoxyribonucleotide containing a hairpin loop made of a hexaethylene glycol chain: conformation and stability. Nucleic Acids Res. Nov. 11, 1990;18(21):6353-9.
Elghanian et al., Selective colorimetric detection of polynucleotides based on the distance-dependent optical properties of gold nanoparticles. Science. Aug. 22, 1997;277(5329):1078-81.
Eltekova et al., Adsorption of aromatic compounds from solutions on titanium dioxide and silica. Langmuir 1987; 3(6): 951-957.
Englisch et al., Chemically Modified Oligonucleotides as Probes and Inhibitors. Angewandte Chemie, International Edition 1991; 30: 613-629.
Enustun et al., Coagulation of Colloidal Gold. J. Am. Chem. Soc. 1963; 85 (21): 3317-3328.
Fattal et al., Biodegradable polyalkylcyanoacrylate nanoparticles for the delivery of oligonucleotides. J Control Release. Apr. 30, 1998; 53(1-3):137-43.
Ferentz et al., Disulfide-crosslinked oligonucleotides. J. Am. Chem. Soc. 1991; 113(10): 4000-4002.
Freier et al., The ups and downs of nucleic acid duplex stability: structure-stability studies on chemically-modified DNA:RNA duplexes. Nucleic Acids Res. Nov. 15, 1997;25(22):4429-43.
Frens, Nature Phys. Sci., 241, 20 (1973).
Grabar et al., Preparation and Characterization of Au Colloid Monolayers. Anal. Chem. 1995; 67(4): 735-743.
Hayashi, Ultrafine particles. Journal of Vacuum Science & Technology A 1987;5(4):1375-1384.
Hayashi, Ultrafine particles. Physics Today 987; 40(12):44-5.
Hayat, M. A. (ed.) Colloidal Gold: Principles, Methods, and Applications vol. 1-3 (Academic Press, San Diego, 1989-1991).
He et al., Colloidal Au-Enhanced Surface Plasmon Resonance for Ultrasensitive Detection of DNA Hybridization. J Am Chem Soc 2000 122 (38), 9071-9077.
Henglein et al., Absorption Spectrum and Some Chemical Reactions of Colloidal Platinum in Aqueous Solution. J. Phys. Chem. 1995; 99(38): 14129-14136.
Henglein, Mechanism of reactions on colloidal microelectrodes and size quantization effects. Top. Curr. Chem. 988; 143:113-180.
Henglein, Small-particle research: physicochemical properties of extremely small colloidal metal and semiconductor particles. Chem. Rev. 1989; 89(8): 1861-1873.
Hickman et al., Combining spontaneous molecular assembly with microfabrication to pattern surfaces: selective binding of isonitriles to platinum microwires and characterization by electrochemistry and surface spectroscopy. J. Am. Chem. Soc. 1989; 111(18): 7271-7272.
Hubbard, Electrochemistry of well-defined surfaces. Acc. Chem. Res. 1980: 13(6): 177-184.
Iler, The Chemistry of Silica, Chapter 6, (Wiley 1979).
Jason et al., Toxicology of antisense therapeutics. Toxicol Appl Pharmacol. Nov. 15, 2004;201(1):66-83.
Jen et al., A nonviral transfection approach in vitro: the design of a gold nanoparticle vector joint with microelectromechanical systems. Langmuir. Feb. 17, 2004;20(4):1369-74.
Jschke et al., Tetrahedron Lett. 1993, 34:301.

Kukowska-Latallo et al., Efficient transfer of genetic material into mammalian cells using Starburst polyamidoamine dendrimers. Proc Natl Acad Sci U S A. May 14, 1996; 93(10):4897-902.
Lebedeva et al., Antisense oligonucleotides: promise and reality. Annu Rev Pharmacol Toxicol. 2001;41:403-19.
Lee et al., Adsorption of ordered zirconium phosphonate multilayer films on silicon and gold surfaces. J. Phys. Chem. 1988; 92(9): 2597-2601.
Liu et al., New poly(d-glucaramidoamine)s induce DNA nanoparticle formation and efficient gene delivery into mammalian cells. J Am Chem Soc. Jun. 23, 2004; 126(24):7422-3.
Lytton-Jean et al., A thermodynamic investigation into the binding properties of DNA functionalized gold nanoparticle probes and molecular fluorophore probes. J Am Chem Soc. Sep. 21, 2005;127(37):12754-5.
Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res. 1993; 21: 2585-2589.
Ma et al., Design and synthesis of RNA miniduplexes via a synthetic linker approach. Biochemistry. Feb. 23, 1993;32(7):1751-8.
Maoz et al., Penetration-controlled reactions in organized monolayer assemblies. 2. Aqueous permanganate interaction with self-assembling monolayers of long-chain surfactants. Langmuir 1987; 3(6): 1045-1051.
Maoz et al., Penetration-controlled reactions in organized monolayer assemblies. 1. Aqueous permanganate interaction with monolayer and multilayer films of long-chain surfactants. Langmuir 1987; 3(6): 1034-1044.
Marinakos et al., (1998) Chem. Mater. 10: 1214-19.
Marinakos et al., Gold Nanoparticles as Templates for the Synthesis of Hollow Nanometer-Sized Conductive Polymer Capsules. Adv. Mater. 1999; 11(1): 34-37).
Martin, A New Access to 2-O-Alkylated Ribonucleosides and Properties of 2-O-Alkylated Oligoribonucleotides. Helv. Chim. Acta 1995; 78: 486-504.
Massart, Preparation of aqueous magnetic liquids in alkaline and acidic media. IEEE Transactions on Magnetics Mar. 1981; 17(2): 1247-1248.
Matteucci et al., Synthesis of deoxyoligonucleotides on a polymer support. J. Am. Chem. Soc. 1981; 103(11): 3185-3191.
Maxwell et al., Self-assembled nanoparticle probes for recognition and detection of biomolecules. J Am Chem Soc. Aug. 14, 2002;124(32):9606-12.
McCurdy et al., Nucleosides & Nucleotides 1991, 10:287.
McManus et al., Gene silencing in mammals by small interfering RNAs. Nat Rev Genet. Oct. 2002;3(10):737-47.
Mirkin et al., A DNA-based method for rationally assembling nanoparticles into macroscopic materials. Nature. Aug. 15, 1996;382(6592):607-9.
MRS Bulletin, Jan. 1990; 15(1): 16-47.
Mucic et al., Synthesis and characterization of DNA with ferrocenyl groups attached to their 5-termini: electrochemical characterization of a redox-active nucleotide monolayer. Chem. Commun. 1996; 4:555-557.
Myers et al., A cyclopentane conformational restraint for a peptide nucleic acid: design, asymmetric synthesis, and improved binding affinity to DNA and RNA. Org Lett. Jul. 24, 2003;5(15):2695-8.
Nam et al., Nanoparticle-based bio-bar codes for the ultrasensitive detection of proteins. Science. Sep. 26, 2003;301(5641):1884-6.
Nielsen et al., Sequence-selective recognition of DNA by strand displacement with a thymine-substituted polyamide. Science. Dec. 6, 1991;254(5037):1497-500.
Nuzzo et al., Spontaneously organized molecular assemblies. 3. Preparation and properties of solution adsorbed monolayers of organic disulfides on gold surfaces. J. Am. Chem. Soc. 1987; 109(8): 2358-2368.
Olshaysky et al., Organometallic synthesis of gallium-arsenide crystallites, exhibiting quantum confinement. J. Am. Chem. Soc. 1990; 112(25): 9438-9439.

Ono et al., DNA triplex formation of oligonucleotide analogues consisting of linker groups and octamer segments that have opposite sugar-phosphate backbone polarities. Biochemistry. Oct. 15, 1991;30(41):9914-2.

Ow Sullivan et al., Development of a novel gene delivery scaffold utilizing colloidal gold-polyethylenimine conjugates for DNA condensation. Gene Ther. Oct. 2003;10(22):1882-90.

Patil et al., DNA-based therapeutics and DNA delivery systems: a comprehensive review. AAPS J. Apr. 8, 2005;7(1):E61-77.

Richardson et al., Tethered oligonucleotide probes. A strategy for the recognition of structured RNA. J. Am. Chem. Soc. 1991; 113(13): 5109-5111.

Rosi et al., Nanostructures in biodiagnostics. Chem Rev. Apr. 2005;105(4):1547-62.

Sandhu et al., Gold nanoparticle-mediated transfection of mammalian cells. Bioconjug Chem. Jan.-Feb. 2002;13(1):3-6.

Sanghvi, Y. S., Chapter 15, Antisense Research and Applications, pp. 274-288, Crooke, S. T. and Lebleu. B., ed., CRC Press, 1993.

Schmid, G. (ed.) Clusters and Colloids (VCH, Weinheim, 1994).

Seela et al., Oligodeoxyribonucleotides containing 1,3-propanediol as nucleoside substitute. Nucleic Acids Res. Apr. 10, 1987;15(7):3113-29.

Soriaga et al., Determination of the orientation of aromatic molecules adsorbed on platinum electrodes. The effect of solute concentration. J. Am. Chem. Soc. 1982: 104(14): 3937-3945.

Stephenson et al., Inhibition of Rous sarcoma viral RNA translation by a specific oligodeoxyribonucleotide. Proc Natl Acad Sci U S A. Jan. 1978;75(1):285-8.

Sundaram et al., Particle-mediated delivery of recombinant expression vectors to rabbit skin induces high-titered polyclonal antisera (and circumvents purification of a protein immunogen). Nucleic Acids Res. Apr. 1, 1996;24(7):1375-7.

The Concise Encyclopedia of Polymer Science and Engineering, pp. 858-859, Kroschwitz, J. I., ed. John Wiley & Sons, 1990.

Thomas et al., Conjugation to gold nanoparticles enhances polyethylenimine's transfer of plasmid DNA into mammalian cells. Proc Natl Acad Sci U S A. Aug. 5, 2003;100(16):9138-43.

Timmons et al., Investigation of Fatty Acid Monolayers on Metals by Contact Potential Measurements. J. Phys. Chem. 1965 ; 69(3): 984-990.

Tkachenko et al., Cellular trajectories of peptide-modified gold particle complexes: comparison of nuclear localization signals and peptide transduction domains. Bioconjug Chem. May-Jun. 2004;15(3):482-90.

Tkachenko et al., Multifunctional gold nanoparticle-peptide complexes for nuclear targeting. J Am Chem Soc. Apr. 23, 2003;125(16):4700-1.

Tondelli et al., Highly efficient cellular uptake of c-myb antisense oligonucleotides through specifically designed polymeric nanospheres. Nucleic Acids Res. Dec. 1, 1998; 26(23):5425-31.

Uchida et al., Gallium arsenide nanocrystals prepared in quinoline. J. Phys. Chem. 1991; 95(14): 5382-5384.

Wang et al., Nanometer-sized semiconductor clusters: materials synthesis, quantum size effects, and photophysical properties. J. Phys. Chem., 1991; 95(2): 525-532.

Wasserman et al., Structure and reactivity of alkylsiloxane monolayers formed by reaction of alkyltrichlorosilanes on silicon substrates. Langmuir 1989; 5(4): 1074-1087.

Weller, Colloidal Semiconductor Q-Particles: Chemistry in the Transition Region Between Solid State and Molecules. Angew. Chem. Int. Ed. Engl. Jan. 1993; 32(1):41-53.

Whitesides, Proceedings of the Robert A. Welch Foundation 39th Conference on Chemical Research Nanophase Chemistry, Houston, Tex., pp. 109-121 (1995).

Zamecnik et al., Inhibition of Rous sarcoma virus replication and cell transformation by a specific oligodeoxynucleotide. Proc Natl Acad Sci U S A. Jan. 1978;75(1):280-4.

Aynie, et al., "Spongelike Alginate Nanoparticles as a New Potential System for the Delivery of Antisense Oligonucleotides," Antisense & Nucleic Acid Drug Development 9:301-312 (1999).

Berton, et al., "Highly loaded nanoparticulate carrier using an hydrophobic antisense oligonucleotide complex," European Journal of Pharmaceutical Science 9:163-170 (1999).

Capaccioli, et al., "Cationic Lipids Improve Antisense Oligonucleotide Uptake and Prevent Degradation in Cultured Cells and inHuman Serum," Biochemical and Biophysical Research Communications, 197(2):818-825 (1993).

Chavany, et al., "Adsorption of Oligonucleotides onto Polyisohexylcyanoacrylate Nanoparticles Protects Them Against Nucleases and Increases Their Cellular Uptake," Pharmaceutical Research, 11(9):1370-1378 (1994).

Chavany, et al., "Polyalkylcyanoacrylate Nanoparticles as Polymeric Carriers for Antisense Oligonucleotides," Pharmaceutical Research 9(4):441-449 (1992).

Chithrani, et al., "Determining the Size and Shape Dependence of Gold Nanoparticle Uptake into Mammalian Cells," Nano Letters 6(4):662-668 (2006).

"Introducing Antisense Oligonucleotides into Cells", Innovation & Precision in Nucleic Acid Synthesis, Integrated DNA Technologies (2005).

Leslie, et al., "A New Tool or Oligonucleotide Import into Cells," Clinical Chemistry 55(4):609-610 (2009).

Maruyama, et al., "Nanoparticle DNA Carrier with Poly(L-lysine) Grafted Polysaccharide Copolymer and Poly(D,L-lactic acid)," Bioconjugate Chem. 8:735-742 (1997).

Miller, et al., "Antisense oligonucleotides: strategies for delivery," PSTT 1(9):377-386 (1998).

Wagner, "Gene inhibition using antisense oligodeoxynucleotides," Nature 372(24):333-335 (1994).

Zimmer, "Antisense Oligonucleotide Delivery with Polyhexylcyanoacrylate Nanoparticles as Carriers," METHODS: A Companion to Methods in Enzymology 18:286-295 (1999).

\* cited by examiner

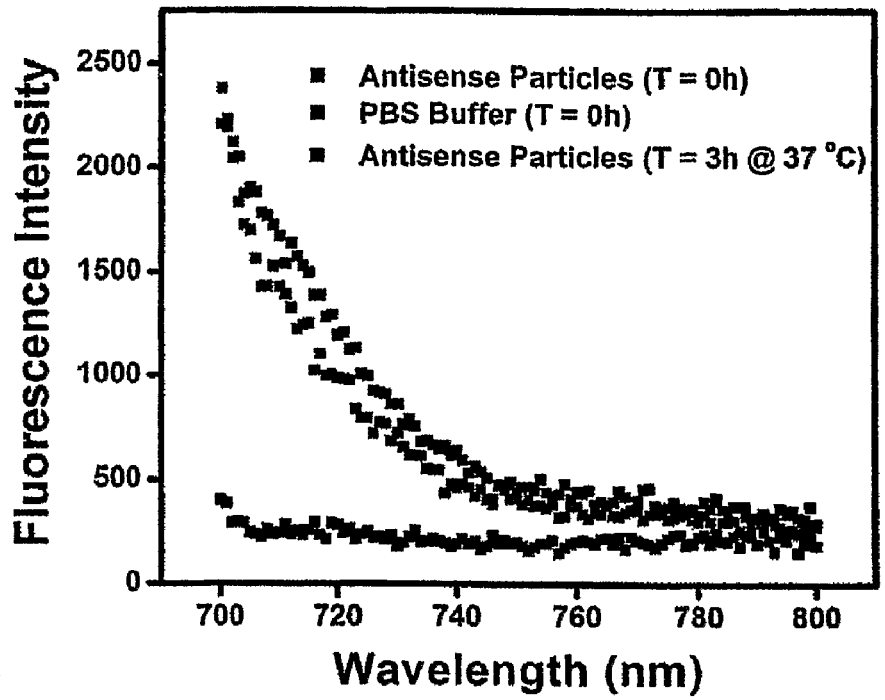

Figure 1

Figure 1. Fluorescence spectra of antisense particles compared to PBS buffer. This indicated that there is some residual fluorescence from the fluorophores on the DNA when the DNA is attached to the gold nanoparticles. Importantly, we do not observe an increase in fluorescence after the particles are incubated for 3 h at 37 °C, which indicates that the particles are thermally stable and the DNA remains on the particles physiological temperatures.

Figure 2 (A) Melting curves of (red) 3 nM $A_{10}$ 15mer nanoparticle probe hybridized to 3 nM 15 mer fluorophore, $T_m = 46\ °C$, and (black) 3 nM 15mer quencher hybridized to 3 nM 15mer fluorophore, $T_m = 40\ °C$.
(B) Thermodynamic analysis of concentration-dependent melting data for $A_{10}$ 15mer nanoparticle/fluorophore and 15mer molecular quencher/fluorophore experiments.

Figure 3 Experimental: Fluorescence spectra of cell lysate solutions from cells that were incubated with antisense particles for 48 h. The spectrum at T = 0h was measured prior to addition of DTT. The spectra at T = 4 h and T =

Figure 4 Control: Fluorescence spectra of cell lysate solutions from cells that were not incubated with antisense particles. The spectrum at T = 0h was measured prior to addition of DTT. The spectra at T = 19 h was after 19 h of incubation with DTT at 37 °C. As expected, no increase in fluorescence was observed.

Figure 5 Images of EGFP expressing NIH-3T3 cells after 24 h incubation with antisense particles. Upper left: channel collecting Cy5.5 fluorescence; Upper right: channel collecting EGFP fluorescence; Bottom left: transmission image of cells; Bottom right: overlay of fluorescence channels onto transmission image.

Figure 6 1 mm sectioning images of EGFP expressing NIH-3T3 cells after 48 h incubation with a) no particles, b) BSA-NP, c) ncDNA-NP, and d) antisense particles.

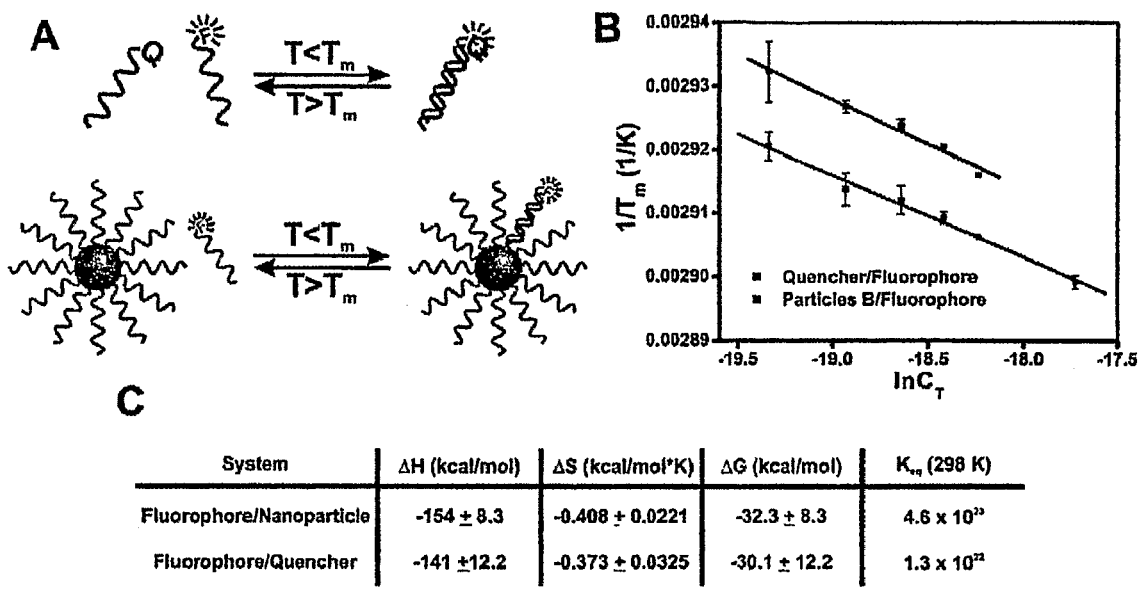

Figure 10

Figure 10 The melting temperature of molecular-quencher modified ASODNs and antisense particle B with complementary fluorophore-labeled target oligonucleotides (A) were measured at various concentrations by monitoring the increase in fluorescence with temperature (B). Thermodynamic analysis of these data (C) revealed that Antisense Particle B has an equilibrium binding constant more than 35 times larger than unmodified ASODNs. Identical experiments were performed using Particles A; it was found that the binding constant for these particles was approximately two times larger than unmodified ASODNs.

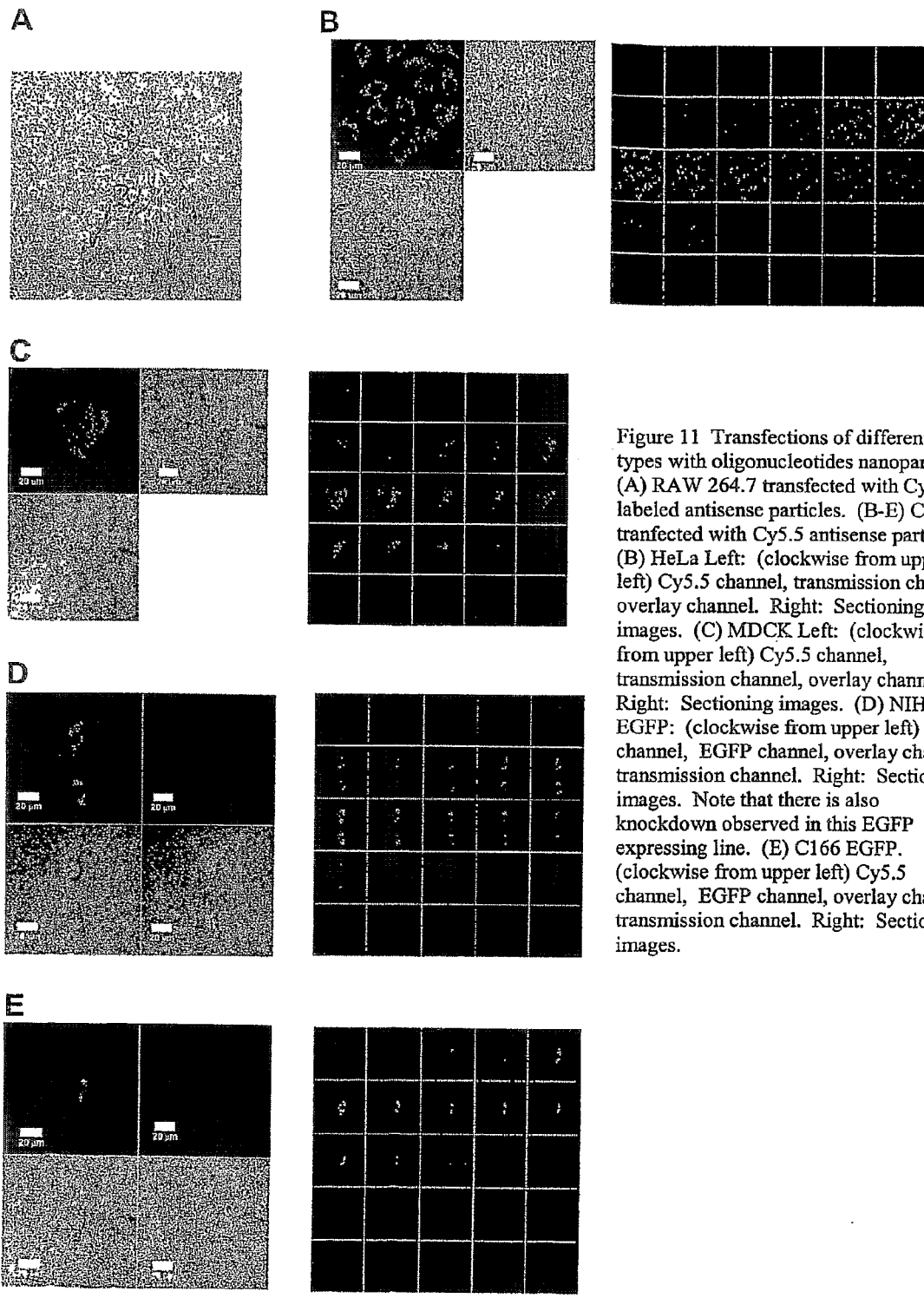

Figure 11 Transfections of different cell types with oligonucleotides nanoparticles. (A) RAW 264.7 transfected with Cy3 labeled antisense particles. (B-E) Cells tranfected with Cy5.5 antisense particles. (B) HeLa Left: (clockwise from upper left) Cy5.5 channel, transmission channel, overlay channel. Right: Sectioning images. (C) MDCK Left: (clockwise from upper left) Cy5.5 channel, transmission channel, overlay channel. Right: Sectioning images. (D) NIH3T3 EGFP: (clockwise from upper left) Cy5.5 channel, EGFP channel, overlay channel, transmission channel. Right: Sectioning images. Note that there is also knockdown observed in this EGFP expressing line. (E) C166 EGFP. (clockwise from upper left) Cy5.5 channel, EGFP channel, overlay channel, transmission channel. Right: Sectioning images.

Figures 11A-11E

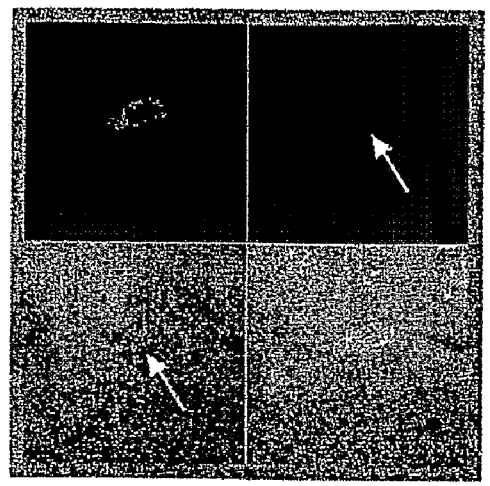

Figure 12

Figure 12 Fluorescent microscopy images of C166-EGFP cells incubated (48 hours) with Antisense Particle A functionalized with fluorophore labeled ASODNs (3' Cy3 and 5' Cy5.5) only reveal fluorescence from Cy5.5 (706-717 nm) (A, upper left). Negligible fluorescence is observed in the emission range of Cy3 (565-615 nm) (A, upper right). Transmission and composite overlay images are shown in the lower left and lower right quadrants, respectively. The arrows indicate the location of the cell.

Figure 13 Fluorescence analysis of lysate before (T = 0 h) and after treatment with DTT (T = 4 h, 19 h).

NUCLEIC ACID FUNCTIONALIZED NANOPARTICLES FOR THERAPEUTIC APPLICATIONS

This application claims benefit of U.S. provisional patent application Ser. No. 60/801,124, filed May 17, 2006, U.S. provisional patent application Ser. No. 60/739,556, filed Nov. 23, 2005, U.S. provisional patent application Ser. No. 60/709,022, filed Aug. 17, 2005, and U.S. provisional patent application Ser. No. 60/690,379, filed Jun. 14, 2005.

This invention was made with government support under grant numbers F49620-01-1-0701 and F49620-01-1-0401, awarded by The Air Force Office of Scientific Research (AFOSR/DURINT), and under grant number EEC-0118025, awarded by The National Science Foundation/Nanoscale Science and Engineering Centers (NSF/NSEC). The government has certain rights in the invention.

BACKGROUND

Nucleic acid-based methods for controlling gene expression have significantly impacted research involving gene pathways and function (Patil, et al., The AAP.SJour, 7, E61 (2005), McManus, et al., Nat. Rev. Genet. 3, 737 (2002), Lebedeva, et al., Annu. Rev. Pharmacol. Toxicol. 41, 403 (2001)). In addition, antisense therapies are potentially powerful candidates for clinical treatments of various ailments, including cancer, HIV/AIDS, and other diseases (Patil, et al., supra., Jason, et al., Toxic. And Appl. Pharm. 201, 66 (2004)). One antisense agent, Vitravene™, is currently used to treat retinitis in AIDS patents (Patil, et al., supra.). In conventional antisense approaches, oligonucleotides designed to hybridize with target mRNA sequences are delivered to a cell in a variety of ways. This hybridization leads to a down-regulation in the expression of the corresponding translated proteins. While the potential of antisense oligodeoxyonucleotides (ASODNs) was recognized over twenty years ago (Stephenson, et al., Proc. Not. Acad. Sci. U.S.A. 75, 285 (1978) Zamecnik, et al., Proc. Nat. Acad. Sci. U.S.A. 75, 280 (1978)), their development into viable therapeutic systems has faced challenges with regard to stable transfection and entry into diverse cell types, toxicity, and low efficacy. To address these fundamental barriers, various transfection agents have been developed to shuttle nucleic acids into cells. These include cationic lipids and polymers, modified viruses, dendrimers, liposomes, and nanoparticles (Patil, et al., supra, Jason, et al., supra., Bharali et al., Proc. Nat. Acad. Sci. U.S.A. 102, 11539 (2005), Bielinska, et al., Bioconjugate Chem. 10, 843 (1999)). Along with developments in delivery platforms, efforts have focused on developing nucleic acid analogs and investigating their potential as ASODNs. These include ODNs having phosphorothioate- or morpholino-modified backbones and peptide nucleic acids (PNAs) (De Mesmaeker, et al., Acc. Chem. Res. 28, 366 (1995), Myers, et al., Org. Lett. 5, 2695 (2003)). In some cases, the modified ASODNs provide enhanced stability in the presence of cellular endo- and exonucleases and stronger binding affinity with complementary sequences. Most antisense experiments use modified ASODNs in combination with a delivery mechanism in order to achieve maximum efficacy. While many combinations of carriers and modified ASODNs show promise, no single system has emerged that is vastly superior to others. Typical methods such as using phosphorothioate ASODNs complexed with cationic lipid carriers are often only useful in serum-free transfectins and are semi-toxic to certain cell types, thus limiting their general utility and their potential in therapeutics.

Gold nanoparticles have proven to be extremely useful for diagnostic and other applications. Detailed studies of gold nanoparticles surface-functionalized with both nucleic acids and proteins demonstrate a number of unique and highly useful characteristics of such structures. For instance, oligonucleotides attached to gold nanoparticles bind more strongly and more specifically to complementary oligonucleotides than do oligonucleotides that are not attached to gold nanoparticles. These observations are, in general, associated with the surface density of the oligonucleotide on the nanoparticle (i.e., surface density). The change in hybridization of the oligonucleotide (bound to a nanoparticle) to a target polynuceltide is reflected in an increase in melting temperature ($T_m$), a sharper melting profile, and/or a decease in the dissociation constant ($K_{diss}$) of the resulting hybridization complex compare to hybridization of the free oligonucleotide and the target polynucleotide. These binding events can furthermore alter the physical, electronic and optical properties of the gold nanoparticles in useful ways such as producing characteristic spectral shifts upon the specific binding of an attached oligonucleotide to its complement. Carbohydrates, lipids and proteins such as antibodies can also be attached to gold nanoparticles either individually or in combination.

To improve upon current methods, there exists a need in the art for an ideal antisense system that would feature high uptake efficiencies across many cell types, high intracellular stability, and a strong binding affinity to target mRNA, while maintaining a very low toxicity to either non-targeted cells when the application requires cell killing, or toward the targeted cells when gene manipulation is desired for other applications.

SUMMARY OF THE INVENTION

In one embodiment, methods of inhibiting expression of a gene product are provided comprising the step of hybridizing a polynucleotide encoding the gene product with one or more oligonucleotides complementary to all or a portion of the polynucleotide, the oligonucleotide being bound to a nanoparticle, wherein hybridizing between the polynucleotide and the oligonucleotide occurs over a length of the polynucleotide with a degree of complementarity sufficient to inhibit expression of the gene product. In one embodiment, the oligonucleotide is covalently bound to the nanoparticle. In various aspects of the methods, the oligonucleotide bound to the nanoparticle and the polynucleotide exhibit at least one property selected from the group consisting of an increased melting temperature ($T_m$), a sharper melting profile, and an increased association (or decreased dissociation) binding constant for hybridization, compared to said oligonucleotide not bound to said nanoparticle and said polynucleotide. In Another aspect, the oligonucleotide is bound to the nanoparticle at a surface density high enough to increase cooperative hybridization to the polynucleotide compared to the same oligonucleotide when not bound to said nanoparticle.

In various aspects, expression of the gene product is inhibited in vivo and expression of the gene product is inhibited in vitro. In different aspects, methods are provided wherein the nanoparticle is metallic, a colloidal metal or selected from the group consisting of a gold nanoparticle, a silver nanoparticle, a platinum nanoparticle, an aluminum nanoparticle, a palladium nanoparticle, a copper nanoparticle, a cobalt nanoparticle, an indium nanoparticle, and a nickel nanoparticle. Methods are also provided wherein the oligonucleotide is bound to said nanoparticle through one or more sulfur linkages.

In various aspects of the methods, the oligonucleotide is about 5 to about 100 nucleotides in length, about 5 to about 90 nucleotides in length. about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length. Methods are provided wherein the oligonucleotide is a DNA oligonucleotide, an RNA oligonucleotide, or a modified form of either a DNA oligonucleotide or an RNA oligonucleotide. Methods are provided in which the oligonucleotide is 100% complementary to the polynucleotide. Methods are also provided wherein thee oligonucleotide is greater than 95% complementary to the polynucleotide, greater than 90% complementary to the polynucleotide, greater than 80% complementary to the polynucleotide, greater than 75% complementary to the polynucleotide, greater than 70% complementary to the polynucleotide, greater than 65% complementary to the polynucleotide, greater than 60% complementary to the polynucleotide, greater than 55% complementary to the polynucleotide, or greater than 50% complementary to the polynucleotide.

Also provided are methods wherein the oligonucleotide includes at least one modified internucleotide linkage, the oligonucleotide is a peptide nucleic acid, the oligonucleotide includes a modified internucleoside linkage which is a phosphorothioate linkage, the oligonucleotide includes at least one modified nucleic acid sugar moiety, and/or the oligonucleotide includes at least one modified nucleic acid.

In various aspects of the methods, the oligonucleotide is bound to the nanoparticle through a 5' linkage and/or the oligonucleotide is bound to the nanoparticle through a 3' linkage. Methods contemplate use of an oligonucleotide which comprises a tandem repeat of identical nucleotide sequences, and in various aspects, the tandem repeat comprises two identical nucleotide sequences, three identical nucleotide sequences, four identical nucleotide sequences, five identical nucleotide sequences, or five or more identical nucleotide sequences. In certain aspects, the identical nucleotide sequences in the tandem repeat are separated by a nucleotide spacer between each identical sequence. In other aspects, the oligonucleotide is bound through a spacer to the nanoparticle. In methods of these aspects, the spacer is an organic moiety, a polymer, a water-soluble polymer, a nucleic acid, a polypeptide, and/or an oligosaccharide.

Consistent with the embodiments described above, methods are also provided wherein two or more identical oligonucleotide sequences and at least one distinct oligonucleotide sequence are bound to the same nanoparticle, either individually bound to the nanoparticle or arranged in a tandem array as described above, with or without spacers as described above.

In other methods provided, the nanoparticle is bound to at least two oligonucleotides having different sequences. In certain aspects, the different sequences hybridize to different regions on the same polynucleotide or the different sequences hybridize to different polynucleotides. Methods are provided wherein the different oligonucleotide sequences are individually bound to the nanoparticle and/or are linked in tandem with each other, wherein only one end of one oligonucleotide sequence is bound to the nanoparticle. In various aspects, the oligonucleotide sequences in tandem comprises two nucleotide sequences, three nucleotide sequences, four nucleotide sequences, five nucleotide sequences, or five or more nucleotide sequences. In certain aspects, the individual nucleotide sequences in the tandem arrangement are separated by a nucleotide spacer between each sequence. In other aspects, the oligonucleotide is bound through a spacer to the nanoparticle. In methods of these aspects, the spacer is an organic moiety, a polymer, a water-soluble polymer, a nucleic acid, a polypeptide, and/or an oligosaccharide.

In methods provided the target polynucleotide is a mRNA encoding the gene product and translation of the gene product is inhibited. Methods are also provided wherein the target polynucleotide is DNA in a gene encoding the gene product and transcription of the gene product is inhibited. In variations of this aspect, the DNA encodes the gene product or the DNA is complementary to a coding region for the gene product. Alternatively, the target DNA is a region or sequence which is necessary for DNA replication.

Methods are also provided wherein the target polynucleotide is a bacterial polynucleotide. In this embodiment, the bacterial polynucleotide is bacterial genomic DNA or RNA transcribed from bacterial genomic DNA.

Methods are also provided wherein the target polynucleotide is a viral polynucleotide. In this embodiment, the viral polynucleotide is viral genomic RNA, the viral polynucleotide is viral genomic DNA, or the viral polynucleotide is RNA transcribed from viral genomic DNA. In another embodiment, the viral polynucleotide is a segment of a viral genome that has been integrated into the genome of another organism.

Methods are also provided wherein the target polynucleotide is a fungal polynucleotide. In this embodiments, the fungal polynucleotide is fungal genomic DNA or the fungal polynucleotide is RNA transcribed from fungal genomic DNA.

In various aspect of the methods provided, expression of the gene product is inhibited by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% compared to expression in the absence of the oligonucleotide.

In other aspects of the methods provided, the nanoparticle ranges from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, or about 1 nm to about 10 nm in mean diameter.

In still other aspects of the methods provided, the oligonucleotide is bound to the nanoparticle at a surface density of at least 10 pmol/cm$^2$, at least 15 pmol/cm$^2$, at least 20 pmol/cm$^2$, at least 10 pmol/cm$^2$, at least 25 pmol/cm$^2$, at least 30 pmol/cm$^2$, at least 35 pmol/cm$^2$, at least 40 pmol/cm$^2$, at least 45 pmol/cm², at least 50 pmol/cm², at least 55 pmol/cm², at least 60 pmol/cm², at least 65 pmol/cm², at least 70 pmol/cm², or at least 75 pmol/cm².

Methods include those wherein expression of the targeted gene product is associated with a disease state.

Methods also include those wherein the nanoparticle is optionally labeled.

Methods also include those wherein the nanoparticle further comprises a targeting molecule.

Also provided are methods wherein the target polynucleotide is a mitochondrial polynucleotide.

In various aspects of the methods, packing density of the oligonucleotides on the surface of the nanoparticle is sufficient to result in cooperative behavior between the nanoparticles.

In other embodiments of this aspect, cooperative behavior between the nanoparticles increases the strength of the binding between the oligonucleotide and the polynucleotide, cooperative behavior between the nanoparticles increases the resistance of the oligonucleotide to degradation, cooperative behavior between the nanoparticles increases the resistance of the oligonucleotide-polynucleotide complex to degradation, and/or cooperative behavior between the nanoparticles increases in the resistance of the oligonucleotide to degradation by a nuclease.

Methods are also provided wherein the target polynucleotide is an inhibitory RNA (including, without limitation, siRNA) that performs a regulatory function, the oligonucleotide is complementary to a regulatory region of the polynucleotide, the oligonucleotide is released from the nanoparticle after the nanoparticle enters a cell, and/or the nanoparticle includes a targeting moiety.

DESCRIPTION OF THE DRAWINGS

FIG. 1. Fluorescence spectra of antisense particles compared to PBS buffer. This indicated that there is some residual fluorescence from the fluorophores on the DNA when the DNA is attached to the gold nanoparticles. An increase in fluorescence after the particles are incubated for 3 hr at 37° C. was not observed, which indicates that the particles are thermally stable and the DNA remains on the particles physiological temperatures.

FIG. 10. The melting temperatures of molecular-quencher-modified ASODNs and antisense particle B with complementary fluorophore-labeled target oligonucleotides (A) were measured at various concentrations by monitoring the increase in fluorescence with temperature (B). Thermodynamic analysis of these data (C) revealed that Antisense Particle B has an equilibrium binding constant more than 35 times larger than unmodified ASODNs. Identical experiments were performed using Particles A; it was found that the binding constant for these particles was approximately two times larger than unmodified ASODNs.

FIG. 11. Transfections of different cell types with oligonucleotides nanoparticles. (A) RAW 264.7 transfected with Cy3 labeled antisense particles. (B-E) Cells transfected with Cy5.5 antisense particles. (B) HeLa Left: (clockwise from upper left) Cy5.5 channel, transmission channel, overlay channel. Right: Sectioning images. (C) MDCK Left: (clockwise from upper left) Cy5.5 channel, transmission channel, overlay channel. Right: Sectioning images. (D) NIH3T3 EGFP: (clockwise from upper left) Cy5.5 channel, EGFP channel, overlay channel, transmission channel. Right: Sectioning images. Note that there is also knockdown observed in this EGFP expressing line. (E) C166 EGFP. (clockwise from upper left) Cy5.5 channel, EGFP channel, overlay channel, transmission channel. Right: Sectioning images.

FIG. 12. Fluorescent microscopy images of C166-EGFP cells incubated (48 hours) with Antisense Particle A functionalized with fluorophore labeled ASODNs (3' Cy3 and 5' Cy5.5) only reveal fluorescence from Cy5.5 (706-717 nm) (A, upper left). Negligible fluorescence is observed in the emission range of Cy3 (565-615 nm) (A, upper right). Transmission and composite overlay images are shown in the lower left and lower right quadrants, respectively. The arrows indicate the location of the cell.

DETAILED DESCRIPTION OF THE INVENTION

Figure 2:
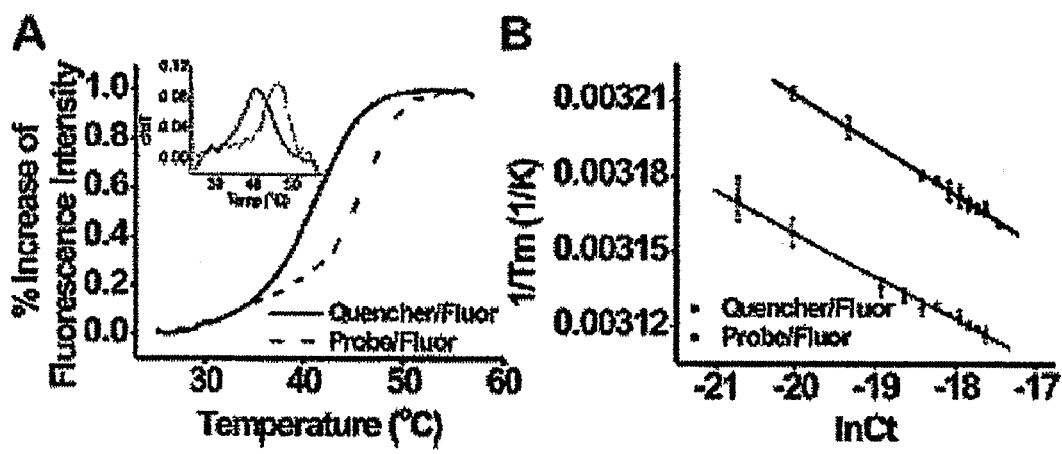
FIG. 2 Melting curves of 3 nM A10 15mer nanoparticle probe hybridized to 3 nM 15mer fluorophore, Tm=46° C., and 3 nM 15mer quencher hybridized to 3 nM 15mer fluorophore Tm=40° C. (B) Thermodynamic analysis of concentration-dependent melting data for A10 15mer nanoparticle/fluorophore and 15mer molecular quencher/fluorophore experiments.

Gold nanoparticles exhibit a variety of unique optical, electronic, and catalytic properties (Daniel, et al., Chem. Rev. 104, 293 (2004)), and owing to their affinity for biomolecules, they have been used extensively in immunostaining (Baudhuin, et al., Colloidal Gold: Principles, Methods, and Applications 2, 1 (1989)), as intracellular targeting agents (Tkachenko et al., Bioconjugate Chem. 15, 482 (2004)), and as non-viral vectors for DNA delivery (Thomas, et al., Proc. Nat. Acad. Sci. 100, 9138 (2003), Sundaram, et al., Nucl. Acids Res. 24, 1375 (1999), Sandhu, et al., Bioconjugate Chem. 13, 3 (2002), Sullivan, et al., Gene Therapy 10, 1882 (2003), Jen et al., Langmuir 20, 1369 (2004)). Developments in the last decade have shown that gold nanoparticles chemically functionalized with alkylthiol-terminated oligonucleotides (Mirkin, et al., Nature 382, 607 (1996)) are highly stable in saline solutions and bind complementary nucleic acids in a very selective and cooperative manner, resulting in equilibrium association constants that can be more than two orders of magnitude greater than those observed for unmodified oligonucleotides and their complements (Lytton-Jean, et al., J Am. Chem. Soc. 12?, 12754 (2005)). These unique properties have made oligonucleotide-functionalized gold nanoparticles the centerpiece of several highly sensitive and selective assays for biomolecule detection (Rosi, et al., Chem. Rev. 105, 1547 (2005), Elghanian, et al., Science 277, 1078 (1997), Nam, et al,. Science 301, 1884 (2003), He et al., J Am. Chem. Soc. 122, 9071 (2000), Maxwell, et al., J Am. Chem. Soc. 124, 9606 (2002)). Due to their demonstrated stability and enhanced binding properties, it was hypothesized that these particles could potentially be used as efficient scavengers of intracellular DNA or RNA. Accordingly, methods are provided wherein oligonucleotide-functionalized gold nanoparticles are intrinsically new antisense agents that rely on the ensemble properties of the nanoparticle-oligonucleotide conjugate.

As is described in US Patent Application 20030147966 and elsewhere, it is also well known in the art that gold nanoparticles can pass through cell and, under suitable conditions, nuclear membranes, thus providing a means for labeling cells and for delivering materials into cells and cell nuclei. The utility of these previous methods is, however, limited by the relative instability of surface modified gold nanoparticles. These limitations have been partially addressed by means such as the inclusion of phosphorothioate linkages in the oligonucleotides attached to the nanoparticles in order to retard the degradation of the oligonucleotides by nucleases and by encapsulating the modified nanoparticles in proteinaceous and other protective sheaths.

The present invention addresses these limitations based upon the observation described herein that the binding constant of a gold nanoparticle-labeled oligonucleotide to its complement and both the in vitro and in vivo stabilities of the gold-labeled oligonucleotide itself are substantially increased if the surface density of oligonucleotides on the gold nanoparticle exceeds a certain threshold. In particular, it is demonstrated herein that modified gold nanoparticles prepared as described herein exhibit exceptional in vitro and in vivo stability, this increased stability finding utility in the delivery of therapeutic agents into cells. In one aspect, a surface density of at least 10 picomoles/cm$^2$ provides stable nanoparticle-oligonucleotide conjugates. However, as the ability of the oligonucleotides of the conjugates to hybridize with nucleic acid and oligonucleotide targets can under certain conditions be diminished if the surface density is too great, the surface density in other aspects is no greater than about 35-40 picomoles/cm$^2$.

The utility of the methods provided is demonstrated by the use of the oligonucleotide-modified gold nanoparticles for the in vivo silencing of the expression of a cellular gene by suppressing the translation of the mRNA produced by that gene. In this application, the increase in the binding constant for gold nanoparticles to their complementary sequences by as much as 200% that results from the present invention is, in contrast to the prior art, such that the replication of the genomic sequence(s) bound to the gold-nanoparticle is completely prevented. This ability to silence gene expression can be used in the treatment of disease states that are characterized by the expression of proteins that are aberrant in structure or location. In certain aspects, the methods provided are used for the delivery of expressible genes, including double stranded polynucleotides, into cells in a manner that avoids the well known limitations of retroviral transduction and mechanical methods such as electroporation or "gene guns" that are employed for similar purposes. The utility of these methods can be further enhanced by modifying the gold nanoparticle such that both oligonucleotides and selective binding agents such as antibodies, lectins or cell-specific recognition elements such as RGD peptides or certain carbohydrates or glycoproteins are attached thereto so long as the oligonucleotide surface density is not reduced below the critical threshold level for stability. These cell-specific recognition elements permit the targeting of the oligonucleotide-modified gold nanoparticle to particular cells or cell types with the corresponding improvement in the efficacy of the treatment. In other aspects, the gold nanoparticles are surface functionalized with imaging contrast agents and, in various embodiments have magnetic cores that impart further advantages with respect to imaging and selective cellular targeting. When functionalized nanoparticles also include a label or imaging agent, entry into a target cell type can be quantitated by visualization or by indirect detection. Quantitation of cell entry permits a precise determination of the number of nanoparticle entering a cell, which in turn allows for precise determination of appropriate dosages fro in vivo administration. In still other aspects, the gold nanoparticles are additionally functionalized with known small molecule therapeutic agents that augment the therapeutic efficacy of co-delivered species on the surface of the nanoparticles (e.g. DNA, proteins, carbohydrates, etc.).

Thus, methods of inhibiting expression of a gene product are provided comprising the step of hybridizing a polynucleotide encoding the gene product with one or more oligonucleotides complementary to all or a portion of the polynucleotide, the oligonucleotide being bound to a nanoparticle, wherein hybridizing between the polynucleotide and the oligonucleotide occurs over a length of the polynucleotide with a degree of complementarity sufficient to inhibit expression of the gene product. Methods wherein expression of the gene product is inhibited in vivo and/or in vitro are contemplated.

In another aspect, methods are provided to introduce a mutation in a polynucleotide of a cell comprising the step of contacting the cell with an oligonucleotide bound to a nanoparticle, wherein the oligonucleotide has a sequence that includes one or more bases that differ from the sequence of a target polynucleotide in the cell, and wherein the oligonucleotide is otherwise sufficiently complementary to the target polynucleotide to permit hybridization to the target polynucleotide, and further wherein hybridization allows for cross-over and/or recombination with the target polynucleotide during replication of the target polynucleotide. In one aspect, replication of the target polynucleotide occurs during cell division. In another aspect, replication of the target polynucleotide occurs during replication of the target polynucleotide which is extrachromosomal. In various embodiments, the mutation which is introduced results in inhibited expression of a gene product encoded by the target polynucleotide, whether through modification of transcriptional and/or translational regulatory sequences in the target polynucleotide, or the mutation corrects one or more bases sequences in the target polynucleotide such that the gene product encoded by the target polynucleotide is expressed having the correct, or "naturally-occurring" amino acid sequence, and/or transcriptional and/or translational regulatory elements.

Nanoparticles

In general, nanoparticles contemplated include any compound or substance with a high loading capacity for an oligonucleotide as described herein, including for example and without limitation, a metal, a semiconductor, and an insulator particle compositions, and a dendrimer (organic versus inorganic).

Thus, nanoparticles are contemplated which comprise a variety of inorganic materials including, but not limited to, metals, semi-conductor materials or ceramics as described in US patent application No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, $TiO_2$, Sn, $SnO_2$, Si, $SiO_2$, Fe, $Fe^{+4}$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshavsky, et al., J. Am. Chem. Soc., 112, 9438 (1990); Ushida et al., J. Phys. Chem., 95, 5382 (1992).

In practice, methods of inhibiting gene expression are provided using any suitable particle having oligonucleotides attached thereto that are in general suitable for use in detection assays known in the art to the extent and do not interfere with complex formation, i.e., hybridization to a target polynucleotide. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Suitable nanoparticles are also commercially available from, for example, Ted Pella, Inc. (gold), Amersham Corporation (gold) and Nanoprobes, Inc. (gold).

Also as described in US patent application No 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent application No 20030147966, nanoparticles contemplated are produced using HAuCl$_4$ and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticle Size

In various aspects, methods provided include those utilizing nanoparticles which range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or amount surface area that can be derivatized as described herein.

Nanoparticle Targeting Agents

In certain embodiments of the methods, the nanoparticle is optionally labeled and in various aspects of these embodiment, the nanoparticle comprises one or more targeting moieties, including but not limited to proteins, including antibodies, peptides, small molecules, anticancer agents, polynucleotide-binding agents, carbohydrates, lipids, ligands for cell surface receptors, and the like. Targeting moieties are useful for delivery of the functionalized nanoparticle to specific cell types and/or organs, as well as sub-cellular locations.

Accordingly, targeting agent contemplated include nuclear localization signals (NLS) and peptide transduction domains, including, for example, SV40 large T NLS, HIV-1 TAT protein NLS, adenovirus NLS, integrin binding domain, oligolysince (each of which is described in (Tkachenko, et al., Bioconjugate Chem (2004) 15:482-490), and adenovirus fiber protein comprising both NLS and receptor-mediated endocytosis (RME) domains (Tkachenko, et al., Am. Chem. Soc. (2003) 125:4700-4701).

Oligonucleotide Features

Oligonucleotides contemplated for attachment to a nanoparticle include those which modulate expression of a gene product expressed from a target polynucleotide. Accordingly, antisense oligonucleotides which hybridize to a target polynucleotide and inhibit translation, siRNA oligonucleotides which hybridize to a target polynucleotide and initiate an RNAse activity (for example RNAse H), triple helix forming oligonucleotides which hybridize to double-stranded polynucleotides and inhibit transcription, and ribozymes which hybridize to a target polynucleotide and inhibit translation, are contemplated.

Each nanoparticle utilized in the methods provided has a plurality of oligonucleotides attached to it. As a result, each nanoparticle-oligonucleotide conjugate has the ability to bind to a plurality of target polynucleotides having a sufficiently complementary sequence. For example, if a specific mRNA is targeted, a single nanoparticle has the ability to bind to multiple copies of the same transcript. In one aspect, methods are provided wherein the nanoparticle is functionalized with identical oligonucleotides, i.e., each oligonucleotide has the same length and the same sequence. In other aspects, the nanoparticle is functionalized with two or more oligonucleotides which are not identical, i.e., at least one of the attached oligonucleotides differ from at least one other attached oligonucleotide in that it has a different length and/or a different sequence. In aspects wherein different oligonucleotides are attached to the nanoparticle, these different oligonucleotides bind to the same single target polynucleotide but at different locations, or bind to different target polynucleotides which encode different gene products Accordingly, in various aspects, a single functionalized nanoparticle may be used a method to inhibit expression of more than one gene product. Oligonucleotides are thus used to target specific polynucleotides, whether at one or more specific regions in the target polynucleotide, or over the entire length of the target polynucleotide as the need may be to effect a desired level of inhibition of gene expression.

Accordingly, the oligonucleotides are designed with knowledge of the target sequence. Methods of making oligonucleotides of a predetermined sequence are well-known. See, for example, Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are contemplated for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Alternatively, oligonucleotides are selected from a library. Preparation of libraries of this type is well know in the art. See, for example, Oligonucleotide libraries: United States Patent Application 20050214782, published Sep. 29, 2005.

In another aspect, methods are provided wherein the oligonucleotide is functionalized to the nanoparticle in such a way that the oligonucleotide is released from the nanoparticle after the nanoparticle enters a cell. In general an oligonucleotides can be release from the surface of a nanoparticle using either chemical methods, photon release (i.e., irradiating cells in which nanoparticles have entered using an electromagnetic wavelengths chosen based on the nanoparticle particle size), and changes in ionic or acid/base environment.

In one aspect of this embodiment, the oligonucleotide is attached to the nanoparticle via an acid-labile moiety and once the functionalized nanoparticle is taken into the cell via, for example, an endosome, acidification of the endosome (a normal part of endosomal uptake) releases the oligonucleotides. This aspect is particular useful in instances where the intent is to saturate the cell with for example, an siRNA and release from the nanoparticle would improve kinetics and resolve potential steric hindrance problems. RNAi for modulating gene expression is well known in the art and generally described in, for example, United States Patent Application 20060019917, United States Patent Application 20060008907 and United States Patent Application 20050059016, the disclosures of which are incorporated herein by reference in their entireties. Preparation of siRNA oligonucleotide libraries is generally described in United States Patent Application 20050197315 the disclosure of which is incorporated herein by reference in its entirety.

Oligonucleotide Length

The term "oligonucleotides" as used herein includes modified forms as discussed herein as well as those otherwise known in the art which are used to regulate gene expression. Likewise, the term "nucleotides" as used herein is interchangeable with modified forms as discussed herein and otherwise known in the art. In certain instances, the art uses the term "nucleobase" which embraces naturally-occurring nucleotides as well as modifications of nucleotides that can be polymerized into a molecule that functions as antisense. Herein, the terms "nucleotides" and "nucleobases" are used interchangeably to embrace the same scope unless otherwise noted.

Nanoparticles for use in the methods provided are functionalized with an oligonucleotide, or modified form thereof, which is from about 5 to about 100 nucleotides in length. Methods are also contemplated wherein the oligonucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24,25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated.

In still other aspects, oligonucleotides comprise from about 8 to about 80 nucleotides (i.e. from about 8 to about 80 linked nucleosides). One of ordinary skill in the art will appreciate that methods utilize compounds of 8, 9, 10, 11, 12, 13, 14, 15, 16, 17, 18, 19, 20, 21, 22, 23, 24,25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotide in length.

Oligonucleotide Complementarity

"Hybridization" means an interaction between two strands of nucleic acids by hydrogen bonds in accordance with the rules of Watson-Crick DNA complementarity, Hoogstein binding, or other sequence-specific binding known in the art. Hybridization can be performed under different stringency conditions known in the art. Under appropriate stringency conditions, hybridization between the two complementary strands could reach about 60% or above, about 70% or above, about 80% or above, about 90% or above, about 95% or above, about 96% or above, about 97% or above, about 98% or above, or about 99% or above in the reactions. It will be understood by those of skill in the art that the degree of hybridization is less significant that a resulting degree of inhibition of gene product expression.

In various aspects, the methods include use of an oligonucleotide which is 100% complementary to the target polynucleotide, i.e., a perfect match, while in other aspects, the oligonucleotide is at least (meaning greater than or equal to) about 95% complementary to the polynucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the oligonucleotide to the extent that the oligonucleotide is able to achieve the desired degree of inhibition of a target gene product.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The percent complementarity is determined over the length of the oligonucleotide. For example, given an antisense compound in which 18 of 20 nucleotides of the antisense compound are complementary to a 20 nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In various aspect, the oligonucleotide has a sequence that introduces or induces changes in secondary structure of the target polynucleotide, including but not limited to one or more loops or hairpin structures.

Oligonucleotide Attachment

Oligonucleotides contemplated for use in the methods include those bound to the nanoparticle through any means. Regardless of the means by which the oligonucleotide is attached to the nanoparticle, attachment in various aspects is effected through a 5' linkage, a 3' linkage, some type of internal linkage, or any combination of these attachments.

In one aspect, the nanoparticles, the oligonucleotides or both are functionalized in order to attach the oligonucleotides to the nanoparticles. Methods to functionalize nanoparticles and oligonucleotides are known in the art. For instance, oligonucleotides functionalized with alkanethiols at their 3'-termini or 5'-termini readily attach to gold nanoparticles. See Whitesides, Proceedings of the Robert A. Welch Foundation 39th Conference On Chemical Research Nanophase Chemistry, Houston, Tex., pages 109-121 (1995). See also, Mucic et al. Chem. Commui. 555-557 (1996) which describes a method of attaching 3' thiol DNA to flat gold surfaces. The alkanethiol method can also be used to attach oligonucleotides to other metal, semiconductor and magnetic colloids and to the other types of nanoparticles described herein. Other functional groups for attaching oligonucleotides to solid surfaces include phosphorothioate groups (see, for example, U.S. Pat. No. 5,472,881 for the binding of oligonucleotide-phosphorothioates to gold surfaces), substituted alkylsiloxanes (see, for example, Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., Anal. Chem., 67, 735-743 for binding of aminoalkylsiloxanes and for similar binding of mercaptoalkylsiloxanes). Oligonucleotides with a 5' thionucleoside or a 3' thionucleoside may also be used for attaching oligonucleotides to solid surfaces. The following references describe other methods which may be employed to attached oligonucleotides to nanoparticles: Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langmuir, 3, 951 (1987) (aromatic carboxylic acids, aldehydes, alcohols and methoxy groups on titanium dioxide and silica); Lec et al., J. Phys. Chem., 92, 2597 (1988) (rigid phosphates on metals).

U.S. patent application Ser. Nos. 09/760,500 and 09/820, 279 and international application nos. PCT/US01/01190 and PCT/US01/10071 describe oligonucleotides functionalized with a cyclic disulfide. The cyclic disulfides in certain aspects have 5 or 6 atoms in their rings, including the two sulfur atoms. Suitable cyclic disulfides are available commercially or are synthesized by known procedures. Functionalization with the reduced forms of the cyclic disulfides is also contemplated.

In certain aspects wherein cyclic disulfide functionalization, oligonucleotides are attached to a nanoparticle through one or more linkers. In one embodiment, the linker comprises a hydrocarbon moiety attached to a cyclic disulfide. Suitable hydrocarbons are available commercially, and are attached to the cyclic disulfides. The hydrocarbon moiety is, in one aspect, a steroid residue. Oligonucleotide-nanoparticle conjugates prepared using linkers comprising a steroid residue attached to a cyclic disulfide are more stable to thiols compared to conjugates prepared using alkanethiols or acyclic disulfides as the linker, and in certain instances, the oligonucleotide-nanoparticle conjugates have been found to be 300 times more stable. In certain embodiments, the two sulfur atoms of the cyclic disulfide are close enough together so that both of the sulfur atoms attach simultaneously to the nanoparticle. In other aspects, the two sulfur atoms are adjacent each other. In aspects where utilized, the hydrocarbon moiety is large enough to present a hydrophobic surface screening the surfaces of the nanoparticle.

In other aspects, a method for attaching oligonucleotides onto a surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with enhanced stability and selectivity. The process comprises providing oligonucleotides, in one aspect, having covalently bound thereto a moiety comprising a functional group which can bind to the nanoparticles. The moieties and functional groups are those that allow for binding (i.e., by chemisorption or covalent bonding) of the oligonucleotides to nanoparticles. For example, oligonucleotides having an alkanethiol, an alkanedisulfide or a cyclic disulfide covalently bound to their 5' or 3' ends bind the oligonucleotides to a variety of nanoparticles, including gold nanoparticles.

Conjugates produced by use of the "aging" step have been found to be considerably more stable than those produced without the "aging" step. Increased density of the oligonucleotides on the surfaces of the nanoparticles is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. In certain aspects, the surface density is at least 15 picomoles/cm$^2$. Since the ability of the oligonucleotides of the conjugates to hybridize with nucleic acid and oligonucleotide targets can be diminished if the surface density is too great, the surface density is, in one aspect, no greater than about 35-40 picomoles/cm$^2$. Regardless, various oligonucleotide densities are contemplated as disclosed herein.

An "aging" step is incorporated into production of functionalized nanoparticles following an initial binding or oligonucleotides to a nanoparticle. In brief, the oligonucleotides are contacted with the nanoparticles in water for a time sufficient to allow at least some of the oligonucleotides to bind to the nanoparticles by means of the functional groups. Such times can be determined empirically. In one aspect, a time of about 12-24 hours is contemplated. Other suitable conditions for binding of the oligonucleotides can also be determined empirically. For example, a concentration of about 10-20 nM nanoparticles and incubation at room temperature is contemplated.

Next, at least one salt is added to the water to form a salt solution. The salt is any water-soluble salt, including, for example and without limitation, sodium chloride, magnesium chloride, potassium chloride, ammonium chloride, sodium acetate, ammonium acetate, a combination of two or more of these salts, or one of these salts in phosphate buffer. The salt is added as a concentrated solution, or in the alternative as a solid. In various embodiments, the salt is added all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time gives the highest surface density of oligonucleotides on the nanoparticles. Suitable ionic strengths can be determined empirically for each salt or combination of salts.

In one aspect, a final concentration of sodium chloride of from about 0.1 M to about 1.0 M in phosphate buffer is utilized, with the concentration of sodium chloride being increased gradually over time.

After adding the salt, the oligonucleotides and nanoparticles are incubated in the salt solution for a period of time to allow additional oligonucleotides to bind to the nanoparticles to produce the stable nanoparticle-oligonucleotide conjugates. As will be described in detail below, an increased surface density of the oligonucleotides on the nanoparticles stabilizes the conjugates. The time of this incubation can be determined empirically. By way of example, in one aspect a total incubation time of about 24-48, wherein the salt concentration is increased gradually over this total time, is contemplated. This second period of incubation in the salt solution is referred to herein as the "aging" step. Other suitable conditions for this "aging" step can also be determined empirically. By way of example, an aging step is carried out with incubation at room temperature and pH 7.0.

The conjugates produced by use of the "aging" are in general more stable than those produced without the "aging" step. As noted above, this increased stability is due to the increased density of the oligonucleotides on the surfaces of the nanoparticles which is achieved by the "aging" step. The surface density achieved by the "aging" step will depend on the size and type of nanoparticles and on the length, sequence and concentration of the oligonucleotides.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

Oligonucleotide Density

Method are provided wherein the oligonucleotide is bound to the nanoparticle at a surface density of at least 10 pmol/$cm^2$, at least 15 pmol/$cm^2$, at least 20 pmol/$cm^2$, at least 25 pmol/$cm^2$, at least 30 pmol/$cm^2$, at least 35 pmol/$cm^2$, at least 40 pmol/$cm^2$, at least 45 pmol/$cm^2$, at least 50 pmol/$cm^2$, or 50 pmol/$cm^2$ or more.

In one aspect, methods are provided wherein the packing density of the oligonucleotides on the surface of the nanoparticle is sufficient to result in cooperative behavior between nanoparticles. Methods include those wherein cooperative behavior between the nanoparticles increases the strength of the binding between the oligonucleotide and the target polynucleotide.

In another aspect, the cooperative behavior between the nanoparticles increases the resistance of the oligonucleotide to degradation, and/or increases the resistance of the oligonucleotide/polynucleotide complex to degradation. In certain aspects, cooperative behavior between the nanoparticles increases in the resistance of the oligonucleotides to degradation by a nuclease.

Oligonucleotide Copies—Same/Different Sequences

The term "oligonucleotide" includes those wherein a single sequence is attached to a nanoparticle, or multiple copies of the single sequence are attached. For example, in various aspects, an oligonucleotide is present in multiple copies in tandem, for example, two, three, four, five, six, seven eight, nine, ten or more tandem repeats.

Alternatively, the nanoparticle is functionalized to include at least two oligonucleotides having different sequences. As above, the different oligonucleotide sequences are in various aspects arranged in tandem and/or in multiple copies. Alternatively, the oligonucleotides having different sequences are attached directly to the nanoparticle. In methods wherein oligonucleotides having different sequences are attached to the nanoparticle, aspects of the methods include those wherein the different oligonucleotide sequences hybridize to different regions on the same polynucleotide. Alternatively, the different oligonucleotide sequences hybridize to different polynucleotides, thereby modulating gene expression from different target polynucleotides.

The oligonucleotides on the nanoparticles may all have the same sequence or may have different sequences that hybridize with different portions of the target polynucleotide. When oligonucleotides having different sequences are used, each nanoparticle may have all of the different oligonucleotides attached to it or the different oligonucleotides are attached to different nanoparticles. Alternatively, the oligonucleotides on each of the nanoparticles may have a plurality of different sequences, at least one of which must hybridize with a portion of the target polynucleotide.

In another aspect, multiple oligonucleotide are bound on a particle which allow for the ability to crosslink target polynucleotide via either inter- or intra-strand links. Crosslinking in this manner potentiates inhibition by various means including steric hindrance.

Spacers

In certain aspect, functionalized nanoparticles are contemplated which include those wherein an oligonucleotide is attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotide in tandem, whether the oligonucleotides have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, or combinations thereof.

In certain aspects, the spacer has a moiety covalently bound to it, the moiety comprising a functional group which can bind to the nanoparticles. These are the same moieties and functional groups as described above. As a result of the binding of the spacer to the nanoparticles, the oligonucleotide is spaced away from the surface of the nanoparticles and is more accessible for hybridization with its target. In instances wherein the spacer is a polynucleotide, the length of the spacer in various embodiments at least about 10 nucleotides, 10-30 nucleotides, or even greater than 30 nucleotides. The spacer may have any sequence which does not interfere with the ability of the oligonucleotides to become bound to the nanoparticles or to the target polynucleotide. The spacers should not have sequences complementary to each other or to that of the oligonucleotides, but may be all or in part complementary to the target polynucleotide. In certain aspects, the bases of the polynucleotide spacer are all adenines, all thymines, all cytidines, all guanines, all uracils, or all some other modified base.

In another embodiment, a non-nucleotide linker of the invention comprises a basic nucleotide, polyether, polyamine, polyamide, peptide, carbohydrate, lipid, polyhydrocarbon, or other polymeric compounds. Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:

5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000, the disclosures of which are all incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In various aspects, linkers contemplated include linear polymers (e.g., polyethylene glycol, polylysine, dextran, etc.), branched-chain polymers (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); lipids; cholesterol groups (such as a steroid); or carbohydrates or oligosaccharides. Other linkers include one or more water soluble polymer attachments such as polyoxyethylene glycol, or polypropylene glycol as described U.S. Pat. Nos: 4,640,835, 4,496,689, 4,301,144, 4,670,417, 4,791,192 and 4,179,337. Other useful polymers as linkers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers.

In still other aspects, oligonucleotide such as poly-A or hydrophilic or amphiphilic polymers are contemplated as linkers, including, for example, amphiphiles (including oligonucletoides).

Types of Oligonucleotides, Including Modified Forms

In various aspects, methods include oligonucleotides which are DNA oligonucleotides, RNA oligonucleotides, or combinations of the two types. Modified forms of oligonucleotides are also contemplated which include those having at least one modified internucleotide linkage. In one embodiment, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization. The oligonucleotide incorporated with the universal base analogues is able to function as a probe in hybridization, as a primer in PCR and DNA sequencing. Examples of universal bases include but are not limited to 5'-nitroindole-2'-deoxyriboside, 3-nitropyrrole, inosine and pypoxanthine.

Modified Internucleoside Linkages

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide".

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to ', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Patent Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

Modified Sugar and Internucleoside Linkages

In still other embodiments, oligonucleotide mimetics wherein both one or more sugar and/or one or more internucleotide linkage of the nucleotide units are replaced with "non-naturally occurring" groups. The bases of the oligonucleotide are maintained for hybridization with the target polynucleotide. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still other embodiments, oligonucleotides are provided with phosphorothioate backbones and oligonucleosides with heteroatom backbones, and including —$CH_2$—NH—O—

$CH_2$—, —$CH_2$—$N(CH_3)$—O—$CH_2$—, —$CH_2$—O—$N(CH_3)$—$CH_2$—, —$CH_2$—$N(CH_3)$—$N(CH_3)$—$CH_2$- and —O—$N(CH_3)$—$CH_2$—$CH_2$- described in U.S. Pat. Nos. 5,489,677, and 5,602,240. Also contemplated are oligonucleotides with morpholino backbone structures described in US Pat. No. 5,034,506.

In various forms, the linkage between two successive monomers in the oligo consists of 2 to 4, desirably 3, groups/atoms selected from —$CH_2$—, —O—, —S—, —$NR^H$, >C=O, >C=$NR^H$, >C=S, —$Si(R")_2$—, —SO—, —$S(O)_2$—, —$P(O)_2$—, —$PO(BH_3)$—, —$P(O,S)$—, —$P(S)_2$—, —$PO(R")$—, —$PO(OCH_3)$—, and —$PO(NHR^H)$, where RH is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=(including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N=(including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$, —O—$CH_2$—S—, —S—$CH_2$—O—, —$CH_2$—$CH_2$—S—, —O—$CH_2$—$CH_2$—S—, —S—$CH_2$—CH=(including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—$S(O)_2$—O—, —O—$S(O)_2$—$CH_2$—, —O—$S(O)_2$—$NR^H$—, —$NR^H$—$S(O)_2$—$CH_2$—; —O—$S(O)_2$—$CH_2$—, —O—$P(O)_2$—O—, —O—$P(O,S)$—O—, —O—$P(S)_2$—O—, —S—$P(O)_2$—O—, —S—$P(O,S)$—O—, —S—$P(S)_2$—O—, —O—$P(O)_2$—S—, —O—$P(O,S)$—S—, —O—$P(S)_2$—S—, —S—$P(O)_2$—S—, —S—$P(O,S)$—S—, —S—$P(S)_2$—S—, —O—$PO(R")$—O—, —O—$PO(OCH_3)$—O—, —O—PO(O $CH_2CH_3$)—O—, —O—PO(O $CH_2CH_2$S—R)—O—, —O—$PO(BH_3)$—O—, —O—$PO(NHR^N)$—O—, —O—$P(O)_2$—$NR^HH$—, —$NR^H$—$P(O)_2$—O—, —O—P (O,$NR^H$)—O—, —$CH_2$—$P(O)_2$—O—, —O—$P(O)_2$—$CH_2$—, and —O—$Si(R")_2$—O—; among which —$CH_2$—CO—$NR^H$—, —$CH_2$—$NR^H$—O—, —S—$CH_2$—O—, —O—$P(O)_2$—O—O—P(—O,S)—O—, —O—$P(S)_2$—O—, —$NR^HP(O)_2$—O—, —O—$P(O,NR^H)$O—, —O—PO(R")—O—, —O—$PO(CH_3)$—O—, and —O—$PO(NHR^N)$O—, where RH is selected form hydrogen and $C_{1-4}$-alkyl, and R" is selected from $C_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. patent application NO. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O—, S—, or N-alkyl; O—, S—, or N-alkenyl; O—, S— or N-alkynyl; or O-alkyl—O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. Other modifications include 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Still other modifications include 2'- methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Bases

Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, Nucleic Acids Research, 1997, vol. 25, pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., Angewandte Chemie, International Edition, 1991, 30, 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Conjugates

Another modification of the oligonucleotides contemplated involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups contemplated include intercalators, reporter molecules, polyamines, polyamides, polyethylene glycols, polyethers, groups that enhance the pharmacodynamic properties of oligonucleotides, and groups that enhance the pharmacokinetic properties of oligonucleotides. Typical conjugate groups include cholesterols, lipids, phospholipids, biotin, phenazine, folate, phenanthridine, anthraquinone, acridine, fluoresceins, rhoda-mines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of the compounds of the present invention. Also contemplated are groups that enhance binding or association of the oligonucleotide or a targeting agent to its target (either the target polynucleotide of target of the targeting agent) by bringing either or both into proximity of the target through association or interaction with the actin/myosin intracellular framework, the early to late endosome framework, the translational to endoplasmic reticulum to golgi network pathway, etc.).

Representative conjugate groups are disclosed in International Patent Application PCT/US92/09196, filed Oct. 23, 1992, and U.S. Pat. No. 6,287,860, the entire disclosures of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glyc-ero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety. See, for example U.S. Pat. Nos. 4,828,979; 4,948,882; 5,218,105; 5,525,465; 5,541,313; 5,545,730; 5,552,538; 5,578,717, 5,580,731; 5,580,731;

5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, the disclosures of which are incorporated herein by reference.

Still other conjugate moieties include proteins, peptides, and peptide mimetics. In one aspect, members from this group of moieties are selected based on their binding specificity to a ligand expressed in or on a target cell type or a target organ. Alternatively, moieties of this type include a receptor for a ligand on a target cell (instead of the ligand itself), and in still other aspects, both a receptor and its ligand are contemplated in those instances wherein a target cell expresses both the receptor and the ligand. In other aspects, members from this group are selected based on their biological activity, including for example enzymatic activity, agonist properties, antagonist properties, multimerization capacity (including homo-multimers and hetero-multimers). With regard to proteins, conjugate moieties contemplated include full length protein and fragments thereof which retain the desired property of the full length proteins. Fusion proteins, including fusion proteins wherein one fusion component is a fragment or a mimetic, are also contemplated. This group also includes antibodies along with fragments and derivatives thereof, including but not limited to Fab' fragments, F(ab)$_2$ fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

Chimerics

It is not necessary for all positions in a given compound to be uniformly modified, and in fact more than one of the aforementioned modifications may be incorporated in a single compound or even at a single nucleoside within an oligonucleotide. These "chimeric" antisense compounds typically contain at least one region including a modification as described herein, while the remainder of the oligonucleotide remains "unmodified."

In certain aspects, the modification confers increased resistance to nuclease degradation, increased cellular uptake, increased stability and/or increased binding affinity for the target nucleic acid. In other aspects the modification serves as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric compounds may be formed as composite structures of two or more oligonucleotides, modified oligonucleotides, oligonucleosides and/or oligonucleotide mimetics as described above. Such compounds have also been referred to in the art as hybrids or gapmers. See, for example, U.S. Pat. No. 5,013,830; 5,149,797; 5,220,007; 5,256,775; 5,366,878; 5,403,711; 5,491,133; 5,565,350; 5,623,065; 5,652,355; 5,652,356; and 5,700,922, the disclosures of which are incorporated herein by reference in their entireties.

Target Polynucleotides

In various aspects, the target polynucleotide is either eukaryotic, prokaryotic, or viral.

In various embodiments, methods provided include those wherein the target polynucleotide is a mRNA encoding a gene product and translation of the gene product is inhibited, or the target polynucleotide is DNA in a gene encoding a gene product and transcription of the gene product is inhibited. In methods wherein the target polynucleotide is DNA, the polynucleotide is in certain aspects DNA which encodes the gene product being inhibited. In other methods, the DNA is complementary to a coding region for the gene product. In still other aspects, the DNA encodes a regulatory element necessary for expression of the gene product. "Regulatory elements" include, but are not limited to enhancers, promoters, silencers, polyadenylation signals, regulatory protein binding elements, regulatory introns, ribosome entry sites, and the like. In still another aspect, the target polynucleotide is a sequence which is required for endogenous replication.

The terms "start codon region" and "translation initiation codon region" refer to a portion of an mRNA or gene that encompasses contiguous nucleotides in either direction (i.e., 5' or 3') from a translation initiation codon. Similarly, the terms "stop codon region" and "translation termination codon region" refer to a portion of such an MRNA or gene that encompasses contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the oligonucleotides on the functionalized nanaoparticles.

Other target regions include the 5' untranslated region (5'UTR), the portion of an mRNA in the 5' direction from the translation initiation codon, including nucleotides between the 5' cap site and the translation initiation codon of an MRNA (or corresponding nucleotides on the gene), and the 3' untranslated region (3'UTR), the portion of an MRNA in the 3' direction from the translation termination codon, including nucleotides between the translation termination codon and 3' end of an MRNA (or corresponding nucleotides on the gene). The 5' cap site of an MRNA comprises an N7-methylated guanosine residue joined to the 5'-most residue of the MRNA via a 5'-5' triphosphate linkage. The 5' cap region of an MRNA is considered to include the 5' cap structure itself as well as the first 50 nucleotides adjacent to the cap site.

For prokaryotic target polynucleotides, in various aspects, the polynucleotide is genomic DNA or RNA transcribed from genomic DNA. For eukaryotic target polynucleotides, the polynucleotide is an animal polynucleotide, a plant polynucleotide, a fungal polynucleotide, including yeast polynucleotides. As above, the target polynucleotide is either a genomic DNA or RNA transcribed from a genomic DNA sequence. In certain aspects, the target polynucleotide is a mitochondrial polynucleotide. For viral target polynucleotides, the polynucleotide is viral genomic RNA, viral genomic DNA, or RNA transcribed from viral genomic DNA.

Desired Inhibition Results

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of an oligonucleotide-functionalized nanoparticle. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of nanoparticle and a specific oligonucleotide.

Kits

Also provided are kits for inhibiting gene expression from a target polynucleotide. In one embodiment, the kit comprises at least one container, the container holding at least one types of nanoparticles as described herein having one or more oligonucleotides as described here attached thereto. The oligonucleotides on the first type of nanoparticles have one or more sequences complementary (or sufficiently complementary as disclosed herein) to one or more sequences of a first portion of a target polynucleotide. The container optionally includes one or more additional type of nanoparticles which have a sequence complementary to one or more sequence of a second portion of the target polynucleotide.

In another embodiment, the kit comprises at least two containers. The first container holds one or more nanoparticles as disclosed herein having one or more oligonucleotides as described herein attached thereto which have a sequence complementary to one or more sequence of a portion of a target polynucleotide. The second container holds one or more nanoparticles having one or more oligonucleotides attached thereto which have a sequence complementary to one or more sequences of the same or a different portion of the target polynucleotide.

In another embodiment, the kits have oligonucleotides and nanoparticles in separate containers, and the oligonucleotides are to attached to the nanoparticles prior to use for inhibiting gene expression. In one aspect, the oligonucleotides and/or the nanoparticles are functionalized so that the oligonucleotides can be attached to the nanoparticles. Alternatively, the oligonucleotides and/or nanoparticles are provided in the kit without functional groups, in which case they must be functionalized prior to performing the assay.

In various aspects of the kits provided, oligonucleotides include a label or the kit includes a label which can be attached to the oligonucleotides. Alternatively, the kits include labeled nanoparticles or labels which can be attached to the nanoparticles. In each embodiment, the kit optionally includes instructions, each container contains a label, the kit itself includes a label, the kit optionally includes one or more non-specific oligonucleotides (either attached to nanoparticles or not attached to nanoparticles).

EXAMPLES

Example 1

A. Preparation of Gold Nanoparticles

Citrate-stabilized 13 nm gold nanoparticles were prepared by reduction of HAuCl4 with citrate as described in Frens, Nature Phys. Sci., 241, 20 (1973) and Grabar, Anal. Chem., 67, 735 (1995). Briefly, all glassware was cleaned in aqua regia (3 parts HCl, 1 part HNO3), rinsed with Nanopure H2O, then oven dried prior to use. HAuCl4 and sodium citrate were purchased from Aldrich Chemical Company. An aqueous solution of HAUC14 (1 mM, 500 mL) was brought to a reflux while stirring, and then 50 mL of a 38.8 mM trisodium citrate solution was added quickly, resulting in a change in solution color from pale yellow to deep red. After the color change, the solution was refluxed for an additional fifteen minutes, allowed to cool to room temperature, and subsequently filtered through a Micron Separations Inc. 0.45 micron nylon filter. Au colloids were characterized by UV-vis spectroscopy using a Hewlett Packard 8452A diode array spectrophotometer and by Transmission Electron Microscopy (TEM) using a Hitachi 8100 transmission electron microscope. A solution of 13 nm diameter gold particles exhibits a characteristic surface plasmon band centered at 518-520 nm. that is useful in verifying the preparation of these particles.

B. Synthesis Of Oligonucleotides

The oligonucleotide 3' (DTPA)2A10-CTG-CCTG-TCG-CAC-GTC-GAG-Cy5.55' (DPTA=dithiolphosphoramidite) with the first two adenines at the 3' end and the terminal adenine and guanine at the 5" end having phosphorthioate linkages, was synthesized on a 1 micromole scale using a Milligene Expedite DNA synthesizer in single column mode using phosphoramidite chemistry. (Eckstein, F. (ed.) Oligonucleotides and Analogues: A Practical Approach (IRL Press, Oxford, 1991)). All solutions were purchased from Glen Research (DNA synthesis grade). Average coupling efficiency varied from 98 to 99.8%. The underlined portion of this nucleotide sequence is complementary to positions 1198-1215 in the mRNA transcript of pEGFPN-1 (plasmid coding for enhanced green fluorescence protein).

Additionally, the fluorophore Cy5.5 was optionally attached to the 5' end of the oligonucleotide in those cases in which it was desirable to monitor and track the locations of the antisense particles within cells.

C. Preparation of Antisense Gold Nanoparticles

The antisense oligonucleotide (26.2 μg) of Example 1B was added to citrate-stabilized 13 nm gold nanoparticles (1 mL) of Example 1A and shaken overnight at room temperature. A 10% solution of sodium dodecylsulfate (SDS) in nanopure water (10 μL) was then added to the particles followed by 0.1 M phosphate buffer (pH=7.4; 111 μL). Ten aliquots of 2 M NaCl (5.84 μL) were then added to the particles over the course of 48 hours to bring the NaCl concentration to 0.1 M. Prior to use, the particles were washed three times by centrifugation and resuspension in 0.1 M phosphate buffered saline (PBS) containing 0.05 mg/mL BSA. This procedure results in stable particles functionalized with approximately 45 antisense DNA strands per particle corresponding to oligonucleotide surface density of approximately 14 pmol/cm2.

Example 2

A. Detachment of Oligonucleotides from the Nanoparticles In Vitro

At the surface packing densities of oligonucleotides attached to gold nanoparticles in the manner described in Example 1, fluorophores attached to the 5' ends of the oligonucleotides are in sufficiently close proximity to one another as to cause their fluorescence to be partially quenched via intermolecular interactions. Detachment of such fluorophore-labeled oligonucleotides from the nanoparticle from the particle abrogates this fluorescence quenching and will, therefore be manifested as an increase in fluorescence. FIG. 1 shows the fluorescence spectrum of oligonucleotide-coated gold nanoparticles that have been suspended in phosphate-buffered saline (PBS) buffer at 37° C. The emission maximum of the Cy5.5 fluoropbore is approximately 707 nm. The spectra shown in FIG. 1 represent the long-wavelength side of the 707 nm (nominal) Cy5.5 emission peak where changes in emission intensity are most readily detected. The emission intensities of the antisense particles incubated for zero (0) and three (3) hours at 37° C. in phosphate buffer are identical to within the limits of these measurements indicating that the fluorophore-labeled oligonucleotides have been retained on the nanoparticles. Furthermore, essentially no change in fluorescent emissions is observed in fluorophore-labeled antisense particles that have been stored for over six (6) months in PBS.

B. Detachment or Degradation of Oligonucleotides from the Nanoparticles In-Vivo

The in vivo stability of the antisense nanoparticles of the present invention was evaluated using C166 cells (ATCC CRL-2583), a cell line that stably expresses green fluorescent protein EGFP-N1. C166 cells at approximately 30% confluence in Dulbecco's Modified Eagle Medium (DMEM) with 4.5 g/L glucose, 1.5 g/L sodium bicarbonate, and supplemented with 10% fetal bovine serum and 0.2 mg/ml G418 were incubated with antisense nanoparticles (100 nM; 300 μL) prepared as described in Example 1 for 48 hours. The cells were then washed three times with 0.1 M PBS buffer to remove any particles that were not taken up by the cells during the incubation and lysed with 3% SDS in 0.1 M PBS. The lysate was collected and its fluorescence determined. This lysate contains any antisense particles internalized by the cells plus any fluoropbore-labeled oligonucleolides and free fluorophores released therefrom. C116 cells that were not incubated with the nanoparticles were used as a control.

Figure 3:
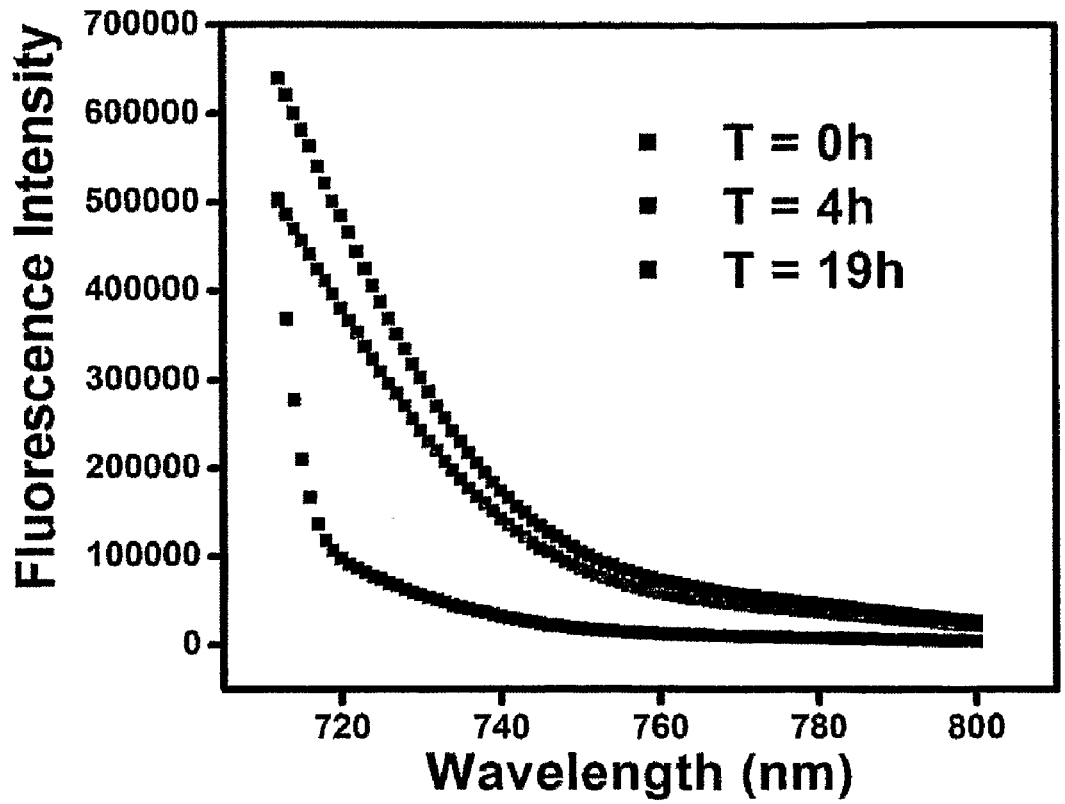
FIG. 3. Experimental: Fluorescence spectra of cell lysate solutions from cells that were incubated with antisense, particles for 48 h. The spectrum at T=0 h was measured prior to addition of DTT. The spectra at T=4 h and T=19 h were after 4 h and 19 h of incubation with DTT at 37° C., respectively. An increase in fluorescence was observed which is consistent with the DNA being displaced from the nanoparticle surfaces by the DTT.
Figure 4:
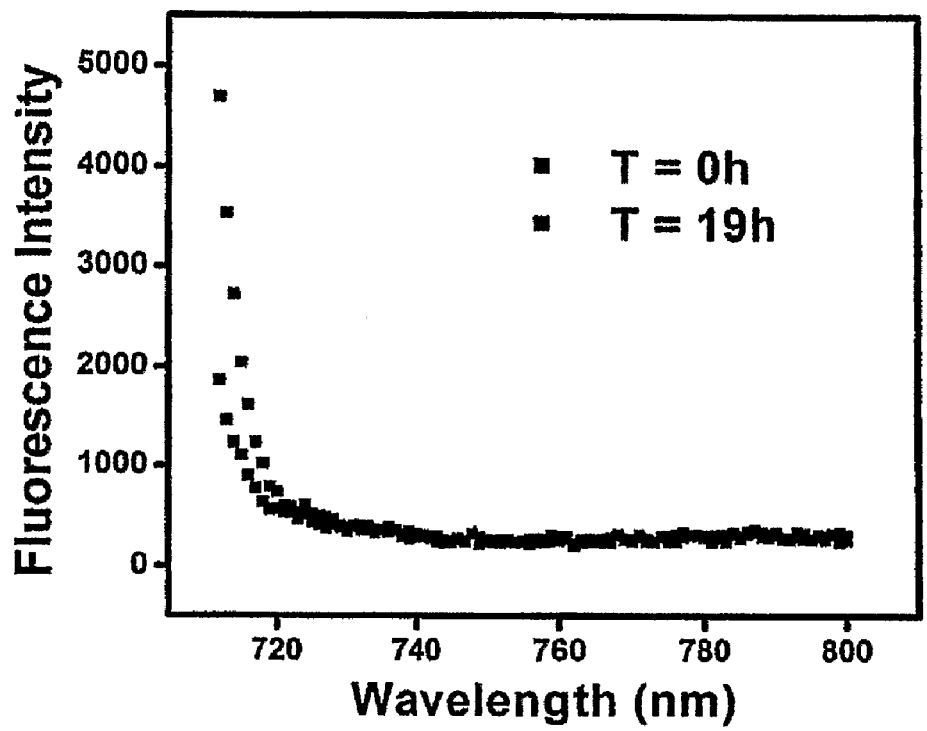
FIG. 4. Control: Fluorescence spectra of cell lysate solutions from cells that were not incubated with antisense particles. The spectrum at T=0 h was measured prior to addition of DTT. The spectrum at T=19 h was after 19 h of incubation with DTT at 37° C. As expected, no increase in fluorescence was observed.

The fluorescence spectrum of the freshly prepared lysate is shown as the bottom curve of FIG. 3. This spectrum is essentially identical to that of the original antisense nanoparticles. The fluorescence spectrum of the corresponding control, which is shown as the bottom curve of FIG. 4, indicates that the intrinsic fluorescence of the lysate does not contribute to any significant extent to the experimental measurements shown in FIG. 3. To determine whether intact antisense nanoparticles were present in the lysate, dithiothreitol (DTT) at a concentration of 0.2 M was added to the lysate and incubated at 37° C., a treatment that is known to release thiol-linked oligonucleotides from gold nanoparticles. The upper two curves of FIG. 3 show the fluorescence spectrum of the lysate after incubation with DTT for 4 and 19 hours, respectively. The substantial increase in fluorescence shown in these two spectra demonstrates the release of fluorophore-labeled oligonucleotides from intact antisense nanoparticles and that, therefore, that the nanoparticles of the present invention are significantly more stable in-vivo than are those of the prior art. The upper curve of FIG. 4 demonstrates that 19 hour incubation of the control lysate with DTT does not result in any significant increase in fluorescence.

Example 3

Figure 5:
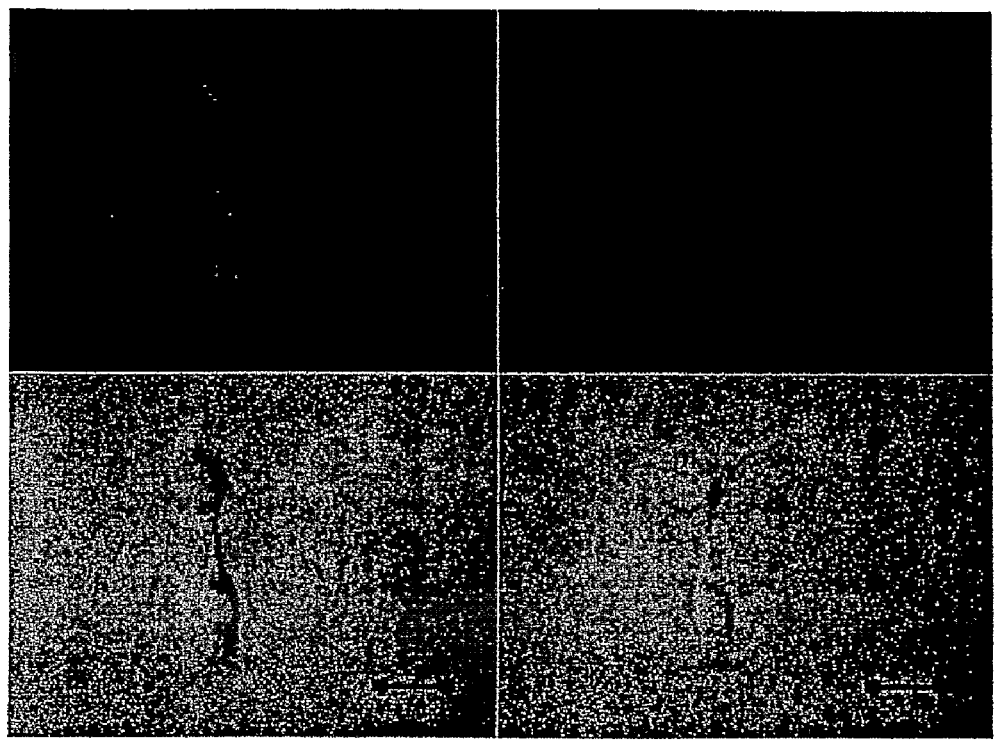
FIG. 5. Images of EGFP expressing NIH-3T3 cells after 24 h incubation with antisense particles. Upper left: channel collecting Cy5.5 fluorescence; Upper right; channel collecting EGFP fluorescence; Bottom left: transmission image of cells; Bottom right: overlay of fluorescence channels onto transmission image.

The ability of the antisense nanoparticles of the present invention to enter into cells was demonstrated by incubating cultures of NIH-3T3 or 066 cells in Dulbecco's Modified Eagle Medium (DMEM) with 4.5 g/L glucose, 1.5 g/L sodium bicarbonate, and supplemented with 10% fetal bovine serum and 0.2 mg/ml G418 with antisense nanoparticles (100 nM; 100 μL) prepared as described in Example 1 for 24 hours at 37° C. and imaging by confocal microscopy (Zeiss Laser Scanning Microscope). The lower left panel in FIG. 5 is a transmitted light image of Nih-3T3 cells after 24 hour incubation with antisense nanoparticles. The upper left panel shows an image of the same cells acquired at 707 nm, the red fluorescence indicating the presence and localization of the antisense nanoparticles in the cell cytoplasm. The upper right panel shows the cells imaged at 540 nm, a wavelength band corresponding to the fluorescence emission from the EGFP produced by the cells. As described in a subsequent example, the antisense oligonucleotides bound to the antisense nanoparticles have suppressed translation of the EGFP mRNA, thus suppressing fluorescence in this channel. The lower right panel of this Figure shows an overlay of the other fluorescence and transmitted light images in this Figure confirming the presence and localization of the antisense nanoparticles in the cytoplasm. In other work, and discussed above, gold nanoparticles alone have been shown to efficiently enter numerous other cell types.

Example 4

The ability of the antisense nanoparticles of the present invention to selectively suppress the translation of mRNA was demonstrated by incubating cultures of NIH-3T3 cells or C166 cells transfected with DNA encoding green fluorescent protein (GFP) in (Dulbecco's Modified Eagle Medium (DMEM) with 4.5 g/L glucose, 1.5 g/L sodium bicarbonate, and supplemented with 10% fetal bovine serum and 0.2 mg/ml G418 with antisense nanoparticles (6.6 nM; 100 μL) for 48 hours at 37° C. Control experiments were performed by incubating the cells with BSA-stabilized gold nanoparticles (BSA-NP), gold nanoparticles to which non-complementary oligonucleotides were attached (ncDNA-NP), or no particles.

Figure 6:
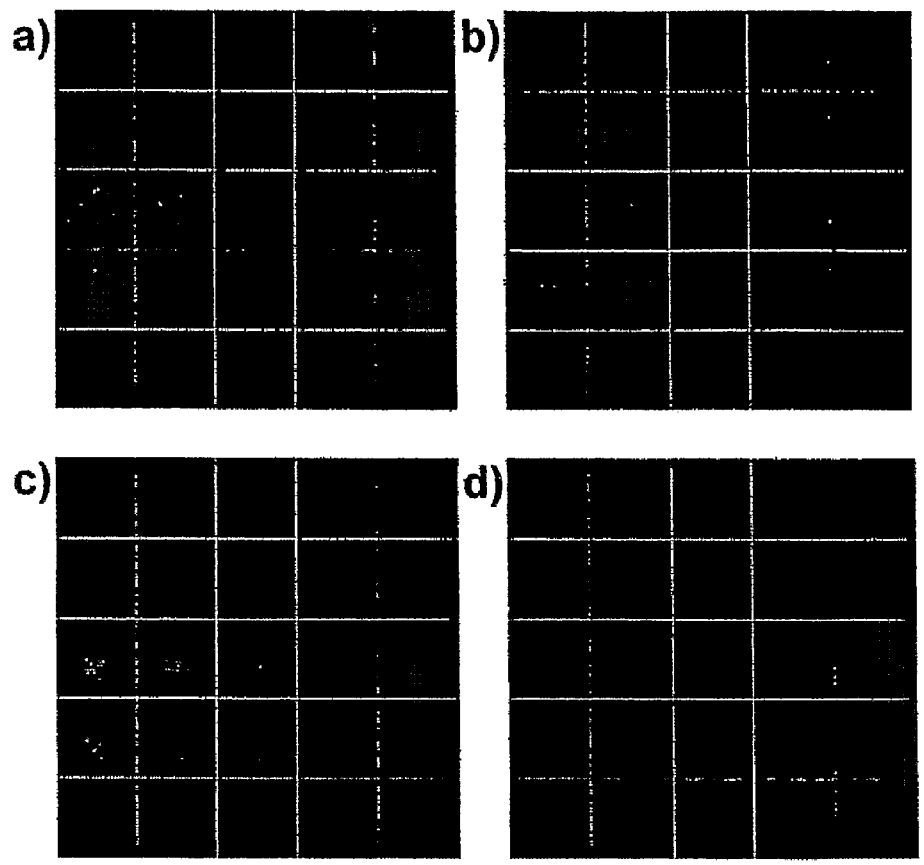
FIG. 6. 1 mm sectioning images of EGFP expressing NIH-3T3 cells after 48 h incubation with a) no particles, b) BSA-NP.c) ncDNA-NP, and d) antisense particles.

FIG. 6 shows depth sectioned confocal microscopy images of these cells. The cells incubated with BSA-NP or ncDNA-NP shown in FIGS. 6b and 6c, respectively, exhibit levels of EGFP fluorescence that are comparable to those exhibited by cells that were not exposed to nanoparticles (FIG. 6a). The level of EGFP fluorescence in cells incubated with antisense nanoparticles (FIG. 6d) is significantly less than the levels exhibited by the controls, thus indicating that the antisense nanoparticles suppressed translation of the EGFP mRNA in these cells. Furthermore, it can be shown that the amount of this suppression depends upon the concentration of antisense nanoparticles in a cell. By way of example, the amount of suppression illustrated in the cells of FIG. 6 after 48 hours of incubation is comparable to the suppression illustrated in FIG. 5 where the cells were incubated with 15 times the concentration of antisense nanoparticles for only 24 hours.

Example 5

In initial experiments, mRNA sequences were targeted coding for enhanced green fluorescent protein (EGFP) expressed in C166, a mouse endothelial cell line (ATCC). In brief, a phosphorothioate-modified antisense sequence complementary to an internal coding region (bases 1198-1215) of the mRNA for EGFP was selected from published literature (26). This sequence was used in the design of two unique sets of antisense gold nanoparticles (Scheme 1), with ASODN conjugated to the gold nanoparticle surface with either one or four thiol groups. Binding of the ASODNs the EGFP coding sequence was then assessed.

The nanoparticles were functionalized with ASODNs that were pre-modified with an A10 tether and either two cyclic disulfides (DTPA) or an alkyl-thiol anchoring group to produce Antisense Particles A and B, respectively.

Oligonucleotides were synthesized on an Expedite 8909 Nucleotide Synthesis System (ABI) using standard solid-phase phosphoramidite methodology. All bases and reagents, including Cy dyes, sulfurizing reagent (3H-1,2-Benzodithiole-3-one1,1-dioxide), and dithiolphosphoroamidite (DTPA) (1,2-Dithiane-4-O-Dimethoxytrityi-5[(2-cyanoethyl)-N,N-diisopropyl)]-phosphoramidite), were purchased from Glen Research. Sulfurizing Reagent was used to generate phosphorothioate linkages between the two terminal 3' adenines and the two terminal 5' bases (see sequences below). Universal CPG was used for the tetra-thiol oligonucleotides while 3' C3H6-thiol CPG (1-O-Dimethoxytrityl-propyl-disulfide, 1'-succinyl-1caa-CPG) was used for the mono-thiol oligonucleotides. All oligonucleotides were purified using published procedures; however, the cyclic disulfide moieties in the tetra-thiol oligonucleotiedes were not cleaved with dithiothreitol (DTT).

Tetra-thiol Oligonucleotides:

```
Antisense:
3'(DTPA)2A-A-AAAAAAAACTGCCGTCGCACGTCG-A-G5'

Nonsense:
3'(DTPA)2A-A-AAAAAAAATTATAACTATTCC-T-A5'
```

Monothiol Oligonucleotides:

```
Antisense:
3'HS(C3H6)A-A-AAAAAAAACTGCCGTCGCACGTCG-G5'

Nonsense:
3'HS(C3H6)A-A-AAAAAAAATTATAACTATTCC-T-A5'

Antisense Oligonucleotide:
3'C-T-GCCGTCGCACGTCG-A-G5'
```

Dual-Fluorophore Oligonucleotides:

```
3'(DTPA)2Cy3A-A-AAAAAAAACTGCCGTCGCACGTCG-AGCy5.55'

3'HS(C3H6)Cy3A-A-AAAAAAACTGCCGTCGCACGTCG-A-GCy5.55'

**Note: hyphens indicate phosphorothioate linkage*
```

Methods described in Gene Therapy Systems company literature (Cytofectin™ product insert) were used to further purify the antisense oligonucleotides. After purification, the oligonucleotides were lyophilized and stored at −78° C. until use.

Thiol-modified or cyclic-disulfide-modified oligonucleotides were added to the nanoparticles (~3 nmol oligonucleotide per 1 ml of 10 nM colloid). After 20 min, SDS (10% solution in NANOpure™ water, 18.2 MΩ) was added to bring the mixture to 0.1% SDS, phosphate buffer (0.1 M; pH=7.4) was added to bring the mixture to 0.01 M phosphate, and sodium chloride (2.0 M solution in NANOpure™ water) was added to bring the NaCl concentration to 0.1 M. The resulting mixture was shaken gently (30 min), after which two more additions of 2.0 M NaCl were added in thirty minute intervals to bring the final mixture to 0.3 M NaCl. This final mixture was gently shaken (24 h) to complete the oligonucleotide ftinctionalization process. The particles were centrifuged (13000 rpm, 20 min.; 3×) and resuspended in 1× PBS (Hyclone).

All binding constant measurements were performed according to published procedures. In these studies, fluorescein was chosen as the molecular fluorophore and Dabcyl was used as the molecular quencher.

The tetra-thiol particle (Particle A) supports 45-50 strands, while the mono-thiol particle (Particle B) has 110-120 strands. While Particle A exhibited a binding constant to its complementary sequence only two times greater than an unmodified ASODN, Particle B had an affinity approximately 35 times stronger than that of the unmodified ASODN (FIG. 10). This result was consistent with a cooperative binding theory, which predicts that higher oligonucleotide packing densities result in a corresponding increase in association constant (27). Taken together, Particles A and B offer the opportunity to study the potential of antisense nanoparticles regulating gene expression, and more specifically, the effect of particle binding constants and oligonucleotide loading on the performance of such particles in the context of EGFP expression.

Oligonucleotide functionalized gold nanoparticles or nanoparticle probes, have become the basis for an increasing number of diagnostic applications that compete with molecular fluorophores in certain settings. For these types of systems, detection relies upon the binding events between a DNA target sequence and the probe sequence. For such an associative equilibrium process, a decrease in target concentration will decrease the amount of duplex formed and, therefore, the melting temperature, Tm, for the system. Thus, the equilibrium binding constant between the target and probe can be a fundamental limiting factor for a high sensitivity detection system that does not involve target amplification. Several studies have qualitatively determined that the presence of gold nanoparticle probes results in cooperative melting properties of the probe/target complex, which both sharpen and increase the melting transition of DNA-linked nanoparticle aggregates. Surprisingly, there have been no thermodynamic studies of such systems aimed at quantifying the differences between the binding properties of molecular fluorophore probes and gold nanoparticle probes. The data herein provides the first study which compares, on a sequence-for-sequence basis, the melting properties of nanoparticle probes and molecular fluorophore probes. These data are the first analytical benchmarks for understanding the fundamental and technological differences between gold nanoparticle probes and molecular fluorophores.

Thermodynamic properties were derived through concentration-dependent melting studies. In a typical experiment, 13 nm diameter Au nanoparticles functionalized with a 5'-thiol-modified 15-base DNA recognition sequence, containing an $A_{10}$ spacer, 1, were allowed to hybridize to one equivalent of a 5'-fluorescein-modified 15-base complementary DNA sequence. The concentrations of the nanoparticle probe and complementary fluorophore sequences were varied while maintaining a 1:1 ratio. To obtain comparable melting data for a molecular quencher/molecular fluorophore system, similar experiments were performed with 2, now acting as the probe, and a complementary 15-base DNA sequence modified with a 3'-dabcyl molecular quencher, 4 (eq 2). All experiments were allowed to equilibrate for over 24 h in 0.3 M NaCl 10 mM PBS buffer. To investigate the effects of the poly-A spacer and the length of the recognition sequence on the binding properties of nanoparticle probes, melting experiments were carried out with multiple types of probes. Poly-A spacers are commonly used to stabilize gold nanoparticle probes and increase their hybridization efficiency by moving the target recognition sequence further from the particle surface. To test the influence of spacers on hybridization thermodynamics, 15-base probes were designed with and without $A_{20}$ spacers, 7 and 8. To investigate the effects of DNA recognition strand length on such properties, nanoparticle probes were designed with an $A_{10}$ spacer and a 21-base recognition sequence, 9. Finally, all of these systems were studied and compared with data from analogous molecular quencher/fluorophore systems with identical recognition sequences.

Binding of nanoparticle probes to a complementary target sequence modified with a molecular fluorophore resulted in quenching and decreased fluorescence intensity. Subsequent heating resulted in dissociation of the probe/target complex and an increase in fluorescence intensity, providing a way to spectroscopically monitor the melting transition (FIG. 2A). Melting temperatures, $T_m$, were determined by talking the maximum of the first derivative of a melting transition measured by fluorescence spectroscopy (FIG. 2A). As the concentration of probe and target increased, a corresponding increase in $T_m$, was observed.

Comparison of the $A_{10}$-15-base nanoparticle/fluorophore and 15-base molecular quencher/fluorophore melting experiments revealed that the nanoparticles typically melted approximately 5° C. higher than the corresponding molecular system. Melting data were analyzed according to literature procedures for molecular systems by graphing $1/T_m$ as a function of concentration according to the following equation:

$$\frac{1}{T_m} = \frac{R}{\Delta H°} \ln C_T + \frac{\Delta S° - R \ln 4}{\Delta H°}$$

where $T_m$ is the melting temperature, R is the gas constant, and $C_T$ is the total concentration of nanoparticles plus fluorophore or quencher plus fluorophore (FIG. 2B and Table 1).

ing strength of the gold nanoparticle probes is due to the high density of DNA bound to the gold surface and not the absolute amount of DNA on a particle probe surface.

The presence of the poly-A spacer is important, as predicted earlier in qualitative analyses. Removal of the A10 spacer dramatically reduced the binding efficiency such that melting transitions were indistinguishable from background fluorescence. On the other hand, increasing the poly-A spacer from A10 to A20 had very little effect on Tm. This demonstrates that there is an optimum distance between the particle and the DNA necessary to achieve the maximum enhancement of the binding strength. In the absence of the poly-A spacer. the DNA strands are close to the particle surface and to each other, reducing the ability of the target sequence to bind to the probe. Introduction of the A10 moves the DNA further away from the particle and alleviates steric hindrance, dramatically increasing the binding strength. Extending the poly-A spacer to A20 does little to affect target binding. Increasing the DNA recognition length dampens the enhanced binding strength provided by the nanoparticles. Analysis of the 21-base nanoparticle/fluorophore and molecular quencher/fluorophore experiments determined equilibrium binding constants of $4.9 \times 10^{18}$ and $2.5 \times 10^{17}$, respectively. This is an enhancement of the nanoparticle binding strength of just over 1 order of magnitude.

It is important to note that in actual detection systems nanoparticle and molecular fluorophore probes would not bind to fluorophore/quencher modified DNA. Our model systems do not account for effects of DNA modification: however, it has been shown that modifications may effect duplex stability in some cases. To test this, the melting properties of

TABLE 1

| Thermodynamic Values of Nanoparticle/Fluorophore and Molecular Quencher/Fluorophore Systems | | | | | |
|---|---|---|---|---|---|
| | 15mer Q/F | $A_{10}$15mer probe/F | $A_{20}$15mer probe/F | 21mer Q/F | $A_{10}$21mer probe/F |
| $\Delta H°$ (kcal/mol) | $-98 \pm 2.0$ | $-117 \pm 3.9$ | $-109 \pm 3.3$ | $-136 \pm 9.7$ | $-144 \pm 3.9$ |
| $\Delta S°$ (kcal/mol-K) | $-0.272 \pm 0.0056$ | $-0.326 \pm 0.011$ | $-0.301 \pm 0.0093$ | $-0.377 \pm 0.027$ | $-0.397 \pm 0.011$ |
| $\Delta G°$ (kcal/mol-K) | $-16.7 \pm 2.0$ | $-19.4 \pm 3.9$ | $-19.2 \pm 3.3$ | $-23.8 \pm 9.7$ | $-25.2 \pm 3.9$ |
| $K_{eq}$ (M$^{-1}$ cm$^{-1}$) at 298 K | $1.8 \times 10^{12}$ | $1.8 \times 10^{14}$ | $1.2 \times 10^{14}$ | $2.8 \times 10^{17}$ | $4.9 \times 10^{18}$ |

Analysis of the A10-15-base probe melting data reveals that the nanoparticle probes have a binding constant of $1.8 \times 10^{14}$, 2 orders of magnitude higher than the binding constant for the molecular quencher/fluorophore system under identical conditions. At room temperature, this translates to binding of the nanoparticles at concentrations as low as 20 fmol. For the equivalent fluorophore probe, the concentration must be increased to at least 2 pmol before target binding will begin to occur.

There are approximately 100 strands of DNA per gold particle (30 pmol/cm$^2$). To determine if the enhanced binding strength of the nanoparticle probes was due to the additional DNA bound to the nanoparticle surface or to some other property unique to the nanoparticles, analogous experiments were performed using 100 nm silica particles functionalized with the same sequence as DNA (Supporting Information, ~200 strands of DNA/particle, 1 pmol/cm$^2$). These particle/fluorophore complexes were found to melt at the same temperature as that of the duplex structures in the case of the molecular quencher/fluorophore experiments. This observation is consistent with the conclusion that the increased bind-duplexes was examined with and without modifications. It was found that overall, the relative binding properties of the nanoparticle and molecular fluorophore probes are not significantly affected (Supporting Information).

From the he results disclosed in this and previous examples, it has been quantitatively determined and compared the thermodynamic values of oligonucleotide functionalized gold nanoparticle probes and molecular fluorophore probes of the same sequence. Nanoparticle probes have a higher binding constant, which increases the sensitivity of assays based upon them, as compared with their molecular counterparts. As the length of the recognition sequence increases, the enhancement of the binding strength diminishes. In designing an effective probe, a balance must be maintained between binding strength and selectivity. Moving to a longer recognition sequence can increase the binding strength but at the cost of selectivity. Nanoparticle probes with a shorter 15-base recognition sequence and the appropriate spacer provide a greater sensitivity than a molecular fluorophore, while maintaining a high selectivity without additional amplification of target sequence.

Example 6

Because the composite properties of the gold nanoparticle-oligonucleotide conjugates are necessary for achieving higher binding constants to complementary sequences, experiments were designed to evaluate their cellular uptake and intracellular stability and specifically studied the fate of the oligonucleotides once the particles were taken up by the cell.

C166, C166-GFP, NIH 3T3, RAW264.7, and HeLa cells were obtained from American Tissue Culture Collection (ATCC) and were grown in 5% CO2 at 37° C. in Dulbecco's modified Eagle's medium (DMEM) supplemented with 10% heat-inactivated FBS. Cells were seeded at a density of 15,000 cells/cm2 and were grown for 24 hours prior to treatment with particles. After 24 hours, the cells were washed with 1× PBS and fresh media was added. The particles (0.024 nmol or 0.048 nmol) were filtered (0.20 μm acetate syringe filter) and added to the media of the freshly washed cells. After 48 hours, the cells were washed in 1× phosphate-buffered saline (PBS) (Hyclone), trypsonized (Trypsin-EDTA), and collected for analysis. Cells were analyzed by a trypan-blue dye (Sigma) to determine percent viability.

For C 166-EGFP cells, NIH-3T3 cells, and HeLa cells, Cy5.5 was used to label the ASODNs on the antisense particles, and therefore identical conditions as described above for Cy5.5 were used. In the case of RAW 264.7 and MDCK cells, Cy3 was arbitrarily chosen to label the particle-bound ASODNs. For these experiments, Cy3 was excited using a HeNe laser source (543 nm) and its emission was collected between 556 and 589 nm.

Entry of the antisense nanoparticles into the EGFP-expressing C166 mouse endothelial cells was confirmed by incubating the cells for 48 h in the presence of particles functionalized with 5' Cy5.5 labeled ASODNs. The uptake was studied using confocal fluorescence microscopy. Observation of Cy5.5 fluorescence throughout the cytoplasm provided proof of particle uptake.

Identical uptake experiments with various cell types, including RAW 264.7 (macrophage), HeLa (cervical carcinoma), NIH-3T3 (fibroblast), and MDCK (kidney) (FIG. 11) were also performed. In each case, greater than 99% efficiency of uptake (virtually every cell incorporated the antisense particles) was observed, and there were no differences in cellular morphology as compared with untreated control cells or cell viability as determined by Trypan Blue staining.

Example 7

To determine whether the ASODNs remain bound to the gold particle surface within the cell, ASODNs labeled with both a 3' fluorophore (Cy3, on the surface of the particle) and a 5' fluorophore (Cy5.5, at the end of the ASODN) were conjugated to the gold nanoparticles. ASODNs remaining stably attached to the particle surface within the cell were expected to show quenching of both the Cy3 and Cy5.5 flourophores. If they were digested by nucleases, it was expected that free Cy5.5 would be seen. If they were displaced from the surface of the particle by chemical reduction, strong emission from both dyes was expected to be seen.

DNAse I was purchased from New England Biolabs Inc. Dabcyl-tagged antisense DNA (having two terminal phosphorothioate linkages on both, ends) was synthesized "in-house" and Alexa Fluor®-tagged complementary DNA was purchased from Integrated DNA Technologies. All stock solutions were prepared by dissolving ultrapure BSA (Arabian) (0.05 mg/mL final concentration), Mg2+ (0.25 mM final concentration), in 0.15 M PBS buffer (pH 7.0) (Hyclone). The following fluorometer settings were used: excitation wavelength, 495 nm; emission wavelength, 520 nm; slit width (all slits), 3 nm; 1 measurement every 30 seconds; assay period, 6000s.

All substrate stock solutions were incubated 6 hr before use and compositions of the substrate stock solutions were as follows: control (Dabcyl-tagged DNA, 900 nM; Alexa Fluor® tagged DNA, 900 nM), Particles A (nanoparticle, 20 nM; Alexa Fluor® tagged DNA, 900 nM), Particles B (nano-partiele, 10 nM; Alexa fluorg® tagged DNA, 900 nM). Reaction mixtures (1 mL) consisted of 50 units DNase I and 10 times diluted substrate stock solution. The change in the fluorescence at 520 nm was measured immediately at room temperature. Fmax was the fluorescence of the reaction mixture (melted DNA) at 80° C., and Fmin was the fluorescence of the reaction mixture at the initial, fully hybridized state.

Figure 7:
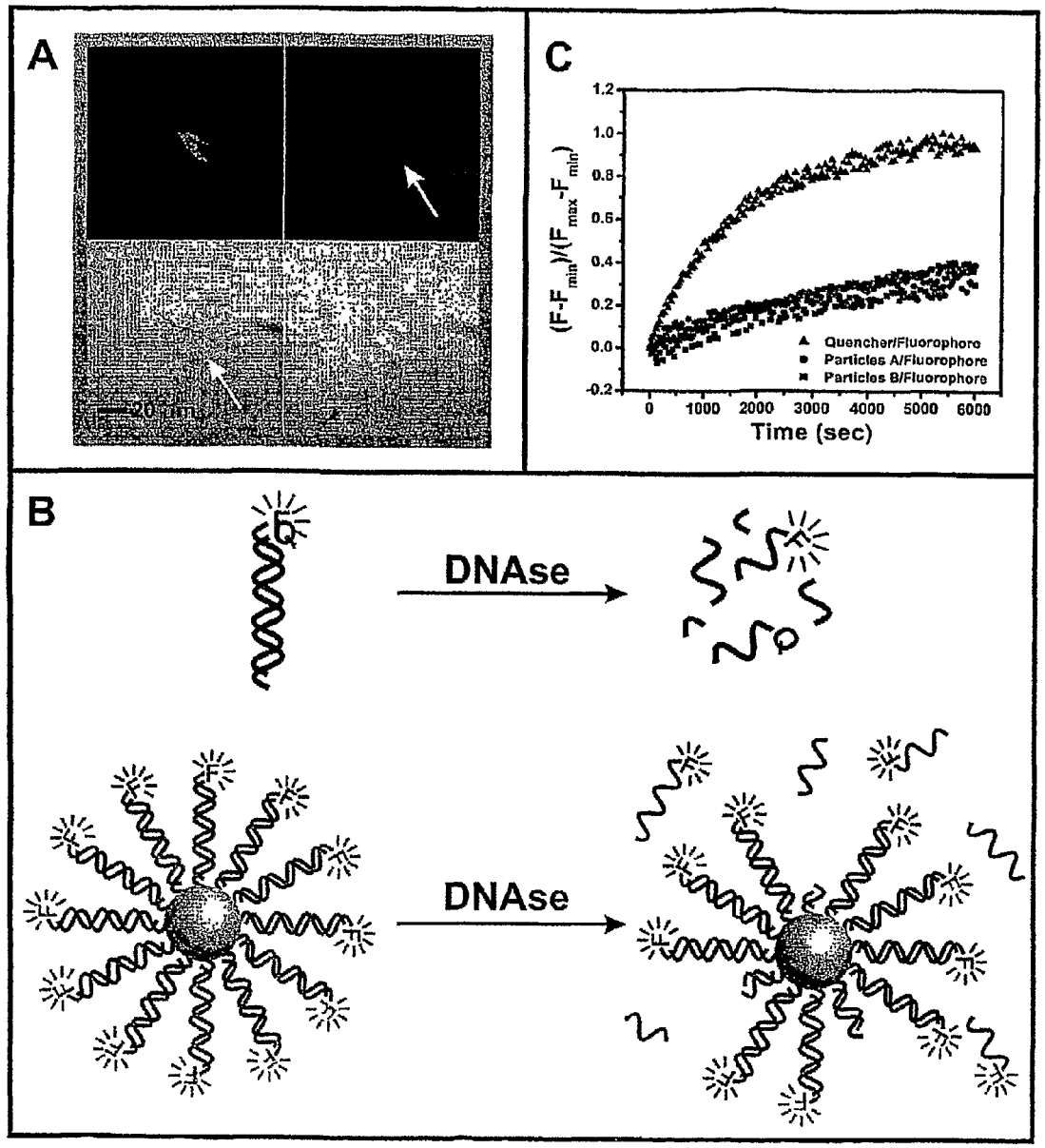
FIG. 7. Experiments aimed at understanding the intracellular stability of antisense nanoparticles. (A) Fluorescent microscopy images of C166-EGFP cells incubated 48 h with Antisense Particle B functionalized with dual-fluorophore labeled ASODNs (3' Cy3 and 5' Cy5.5) only reveal fluorescence from Cy5.5 (706-717 nm, upper left). Negligible fluorescence is observed in the emission range of Cy3 (565-615 nm, upper right). Transmission and composite overlay images are shown in the lower left and lower right quadrants, respectively. The arrows indicate the location of the cell. Similar data collected from experiments using Particle A are included in the Supporting Information (FIG. 12). (B) Duplexes composed of either quencher-modified ASODN/fluorophore-modified complement or antisense particle/fluorophore-modified complement were treated with DNAse. (C) The ASODN duplex degraded much faster than the antisense particle duplex, as calculated using fluorescence spectroscopy where $F_{max}$ is the fluorescence of the mixture at its initial, fully hybridized state and $F_{max}$ is the maximum fluorescence of the system at 80° C. where all of the oligonucleotides are dehybridized.

After a 48 hr incubation period in the presence of particles, two-photon confocal laser scanning microscopy was used to image the cells (FIG. 7). Excitation with both 546 nm and 633 nm light resulted only in fluorescence from the 5' Cy5.5 fluorophore, which could be attributed to some nuclease digestion of the ASODNs and residual fluorescence due to incomplete quenching by the gold nanoparticles (the Cy5.5 is approximately 9 nm from the gold surface). Since negligible 3' Cy3 fluorescence was observed, it was concluded that the ASODNs do, in fact, remain chemically attached to the gold nanoparticle surface while inside the cell.

Figure 13:
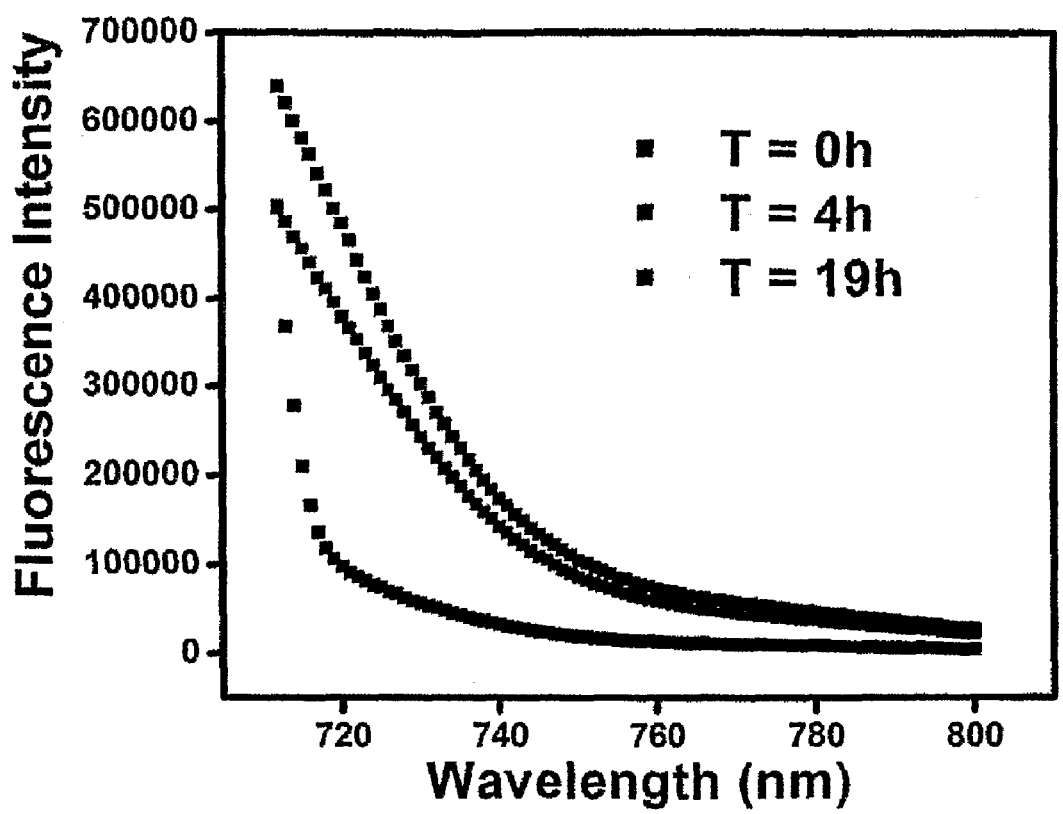
FIG. 13. Fluorescence analysis of lysate before (T=0 h) and after treatment with DTT (T=4 h, 19 h).

In additional experiments, C 166 cells were incubated with antisense particles functionalized with 5' Cy5.5 modified ASODNs. Following a 48 h incubation period, the cells were lysed and the bulk fluorescence of the lysate was measured in the emission range of the Cy5.5 fluorophore (706-717 nm). Dithioltlreitol (DTT) displacement of the Cy5.5-labeled ASODNs from the nanoparticles resulted in increased Cy5.5 fluorescence emission in the lysate, indicating that many of the ASODNs remain undigested by nucleases after 48 h within the cellular environment (FIG. 13).

Example 8

Given the potential for ASODN degradation by nucleases in vivo, in vitro resistance of the antisense particles to DNAse compared to particle-free oligonucleotides was examined.

Remarkably, fluorescent experiments indicated that particle-bound ASODNs are degraded much slower than unbound ASODNs (FIG. 7B,C). This result was likely a reflection of steric inhibition of nuclease degradation due to the tight packing of the ASODNs on the particle surface. Others have made similar observations in the context of assembly and manipulation of oligonucleotide-modified gold nanoparticle superstructures (28). The increased resistance to nuclease degradation of particle-bound ASODNs is a major advantage of such nanoparticles as antisense agents in gene regulation, as it will increase the lifetime of the antisense agent within the cell.

Example 9

The in vivo activity of the antisense particles with respect to gene knockdown was evaluated using EGFP-expressing C166 cells.

Fluorecence was measured using a SpectraMax Gemini EM Microplate Spectroflouormeter (Molecular Devices). Cell samples were lysed in 1× Cell Lysis Buffer (20 mM Tris-HCl (pH 7.5); 150 mM NaCl; 1 mM Na2EDTA; 1 mM EGTA; 1% Triton 2.5 mM) (Cell Signaling Technologies).

Extracted protein samples were placed in 96 well black/clear bottom plates (Costar) and excited at a wavelength of 488 nm. Fluorescence emission was measured by taking the area under the curve from 524-550 nm. All samples were measured in triplicate.

To determine percent knockdown of EGFP, a calibration curve was first generated for each set of samples using lysates of untreated C166-EGFP cells of varying concentrations. Following fluorescence measurements, a BCA assay (Pierce) was performed to determine the protein concentrations of each sample. From these data, a standard curve of fluorescence versus protein concentration was generated. Concurrent with the measurement of the standard fluorescence curve, the fluorescence of the experimental samples were collected (termed "actual" fluorescence). A BCA assay was used to determine the bulk protein concentration of these samples. The protein concentration values were used to extrapolate from the standard calibration curve a "predicted" fluorescence value for each sample. The "predicted" value was compared to the "actual" fluorescence emitted by the sample. The ratio of "actual" fluorescence to "predicted" fluorescence for each sample was normalized to the ratios for the untreated controls to determine percent knockdown.

Cells were grown on a glass coverslip which was placed at the bottom of a 6 well tissue culture plate (Coming). Oligonucleotide-functionalized particles (0.012 mnol) were then added to the wells. Following incubation (48 hours), the cells were washed and mounted on glass slides for imaging. All imaging was performed using two-photon excitation (TPE) laser scanning microscopy on a Zeiss 510 LSM (upright configuration) equipped with a 63× oil-immersion objective (Carl Zeiss, Inc.). In all experiments, the pinhole and gain settings of each individual collection channel were determined using untreated control cells. The settings were held constant throughout the experiment. Sectioning images were obtained at 1 μm intervals.

Cellular EGFP fluorescence from C 166-EGFP cells was excited using an argon laser source at 488 nm and emission was collected between 500 and 550 nm. Cy55 (which was used to label the 5' ends of the ASODNs on the gold nanoparticle) was excited with a HeNe laser source (633 nm), and its emission was collected at a different channel between 706 and 717 nm.

Cellular EGFP fluorescence from C 166-EGFP cells was not collected in this experiment. Cy5.5 (which was used to label the 5' ends of the ASODNs on the gold nanoparticle) was excited with a HeNe laser source (633 nm) and its emission was collected (706-717 nm). Cy3 (which was used to label the 3' ends of the ASODNs on the gold nanoparticle) was excited using a second HeNe laser source (543 nm), and its emission was collected from a separate channel between 565 and 615 nm.

Figure 8:
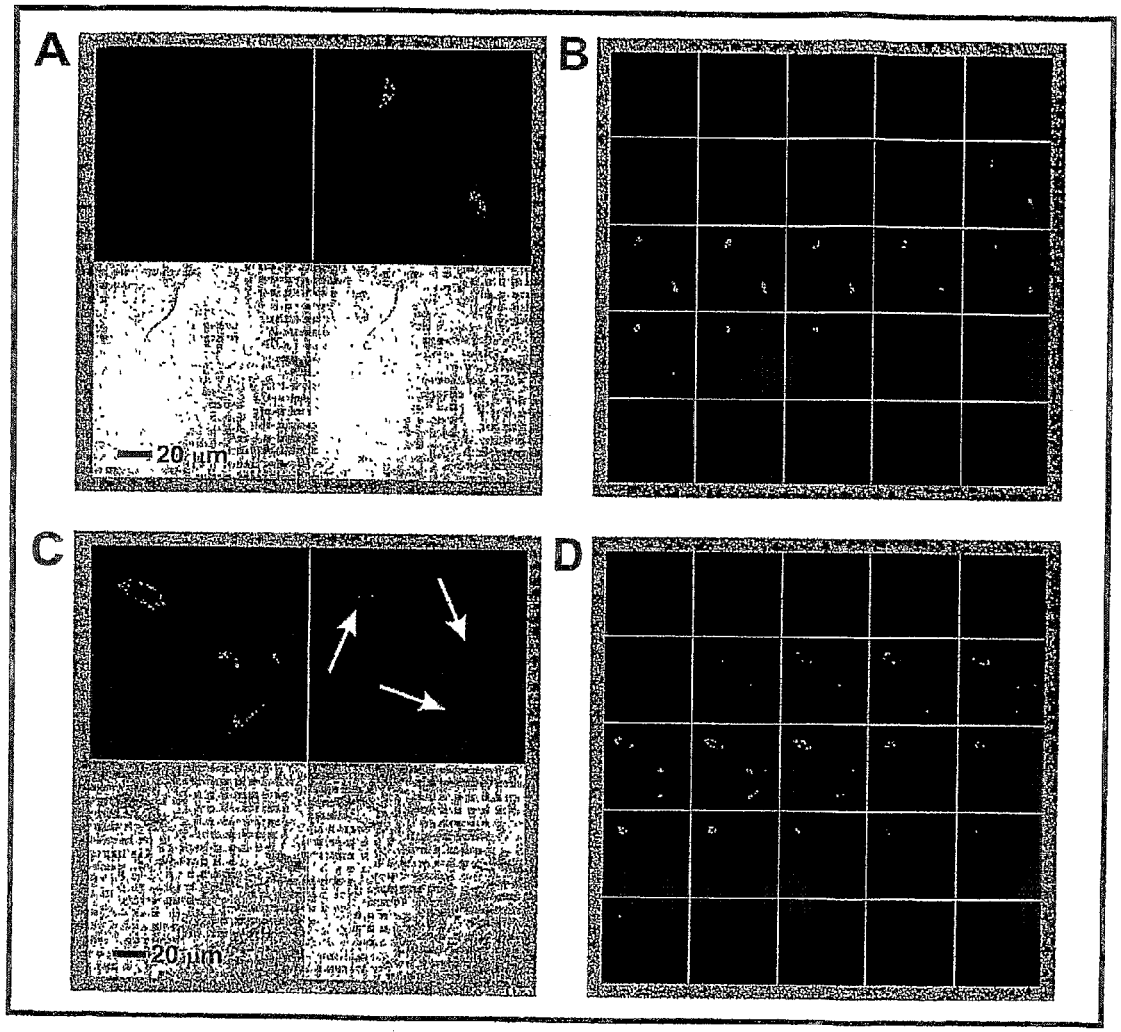
FIG. 8. Confocal fluorescence microscopy images showing EGFP knockdown. (A) Untreated control C166-EGFP cells (upper left Cy5.5 emission, 706-717 nm; upper right EGFP emission, 500-550 mn; lower left, transmission image of cells; lower right, composite overlay of all three channels) showed a significant amount of emission throughout the cell. (B) 1 μm sectioning images of control cells. (C-D) Cells treated with Antisense Particles A or B both showed a decrease in the amount of EGFP emission.

Evidence of EGFP knockdown was first observed by two-photon excitation confocal fluorescence microscopy, which indicated that cells treated with antisense particles exhibited noticeably lower fluorescence compared to untreated control cells (FIG. 8). These observations were then confirmed by quantitatively assaying for EGFP expression using fluorescence spectroscopy. As previously described, the binding properties of the anisense nanoparticles can be tailored by controlling the -number of ASODNs loaded on the particles. It was expected that Particle B. with its higher binding affinity, would cause greater reductions in EGFP expression than Particle A.

Figure 9:
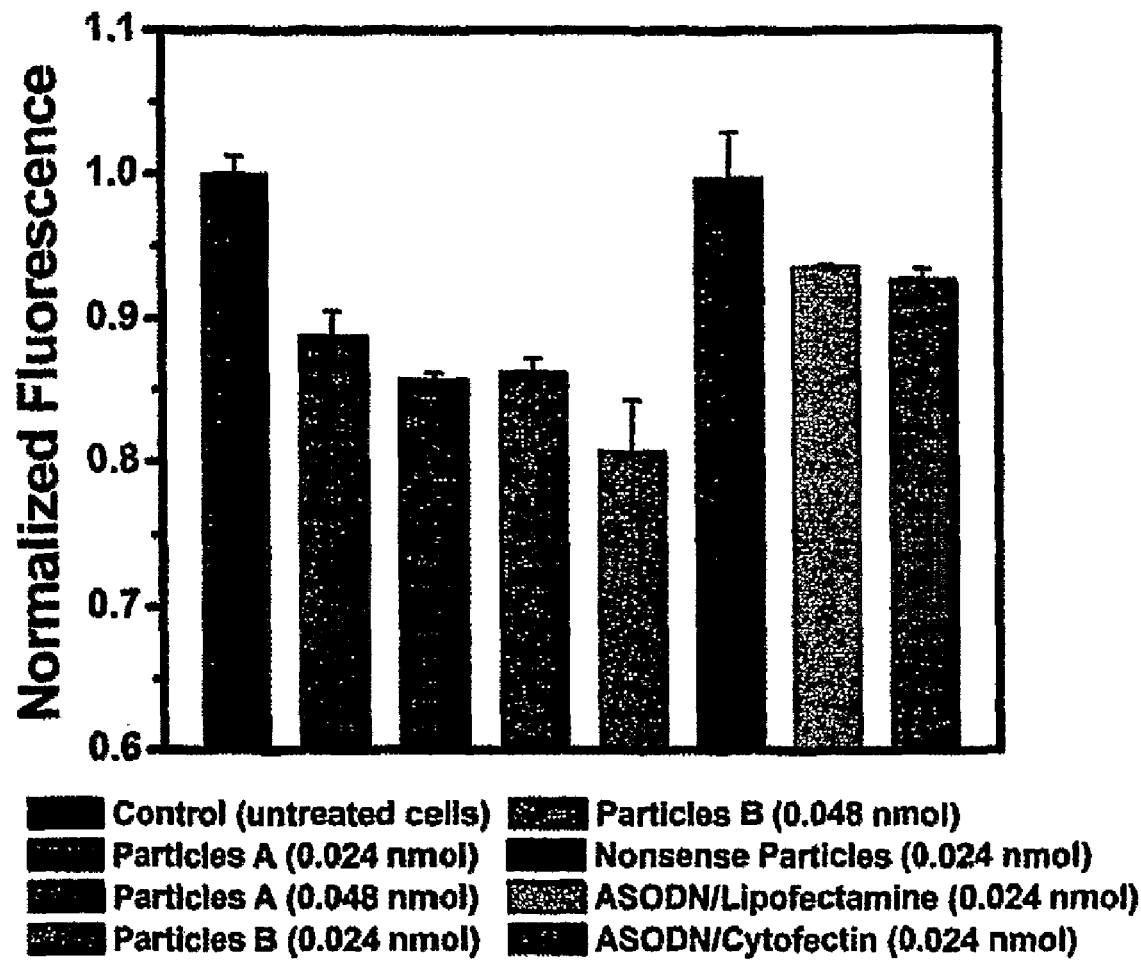
FIG. 9. EGFP knockdown using antisense nanoparticles or Lipoplex/ASODNs complexes. Experiments involving Particle A (tetra-thiol) and Particle B (mono-thiol) show different levels of knockdown. ASODN/Lipoplex systems show less knockdown than antisense particles when compared in a 1:1 fashion.

To test this hypothesis, aliquots of Particle A were added to C166-EGFP cells. After 48 h, the cells were collected, lysed, and assayed for EGFP expression (for quantification methods, see Supporting Information). Non-complementary oligonucleotide functionalized gold nanoparticles (see Supporting Information for sequence) were used as controls and showed similar fluorescence levels to non-treated cells. Cells incubated with 0.024 nmol or 0.048 nmol of Particle A (low binding constant) displayed a 11-12% and 14-15% decreases in EGFP expression, respectively. However, when incubated with the same amount of Particle B (tight binding constant), the cells displayed a decrease in EGFP expression of 13-14% and 19-20%, respectively (FIG. 9). The differences in the observed lnockdown between Particles A and B indicated that the antisense particle binding constant can significantly influence the amount of protein expression.

Example 10

Interestingly, when the particles were compared to commercially available lipoplexes (Lipofectamine™ 2000, Invitrogen; Cytofectin™, Gene Therapy Systems) in the context of EGFP expression, the nanoparticle system out-performed the commercial systems under the conditions studied with respect to percent knockdown, total amotmt of ASODN delivery, and non-toxicity (Table 2).

Following recommended commercial protocols, Lipofectamine™ and Cytofectin™, respectively, were used to transfect EGFP-C166 cells with an equal amount of ASODNs delivered using antisense nanoparticles (0.024 nmol antisense particles:2.64 nmol ASODN); however, extreme toxicity was observed in both cases as measured by cell death. Consequently, the amount of ASODN and transfection reagent was lowered to the point where one strand of transfected ASODN was equivalent to one antisense particle (0.024 nmol antisense particles:0.024 mnol ASODN). In these cases, ASODNs transfected with either Lipofectamine™ or Cytofectin™ only resulted in approximately 6-8% knockdown in EGFP expression (FIG. 9).

TABLE 2

Performance characteristics of antisense nanoparticles compared to lipoplex transfection systems.

| Antisense Experiment | Transfection Efficiency | Observed Toxicity | Approximate Binding Constant | Percent Decrease in EGFP Expression |
|---|---|---|---|---|
| Antisense Particles A (Tetra-Thiol) (0.024 nmol particles; 1.08 nmol ASODN) | >99% (in all cell types tested) | No | $7.1 \times 10^{20}$ | $11 \pm 2$ |
| Antisense Particles A (Tetra-Thiol) (0.048 nmol particles; 2.16 nmol ASODN) | >99% (in all cell types tested) | No | $7.1 \times 10^{20}$ | $14 \pm 0.4$ |

TABLE 2-continued

Performance characteristics of antisense nanoparticles compared to lipoplex transfection systems.

| Antisense Experiment | Transfection Efficiency | Observed Toxicity | Approximate Binding Constant | Percent Decrease in EGFP Expression |
|---|---|---|---|---|
| Antisense Particles B (Mono-Thiol) (0.024 nmol particles; 2.64 nmol ASODN) | >99% (in all cell types tested) | No | $2.6 \times 10^{22}$ | $14 \pm 1$ |
| Antisense Particles B (Mono-Thiol) (0.048 nmol particles; 5.28 nmol ASODN) | >99% (in all cell types tested) | No | $2.6 \times 10^{22}$ | $20 \pm 4$ |
| Nonsense Particles A (0.048 nmol) | N/A | No | N/A | $0 \pm 3$ |
| Nonsense Particles B (0.048 nmol) | N/A | No | N/A | $0 \pm 2$ |
| Lipofectamine ™ 2000 (0.024 nmol ASODN) | >45-99% (Cell-type dependent) | No | $6.7 \times 10^{20}$ | $6 \pm 0.2$ |
| Lipofectamine ™ 2000 (2.64 nmol ASODN) | N/A | Yes | $6.7 \times 10^{20}$ | N/A |
| Cytofectin ™ (0.024 nmol ASODN) | >35-99% (Cell-type dependent) | No | $6.7 \times 10^{20}$ | $7 \pm 0.7$ |
| Cytofectin ™ (2.64 nmol ASODN) | N/A | Yes | $6.7 \times 10^{20}$ | N/A |

Example 11

Figure 14:
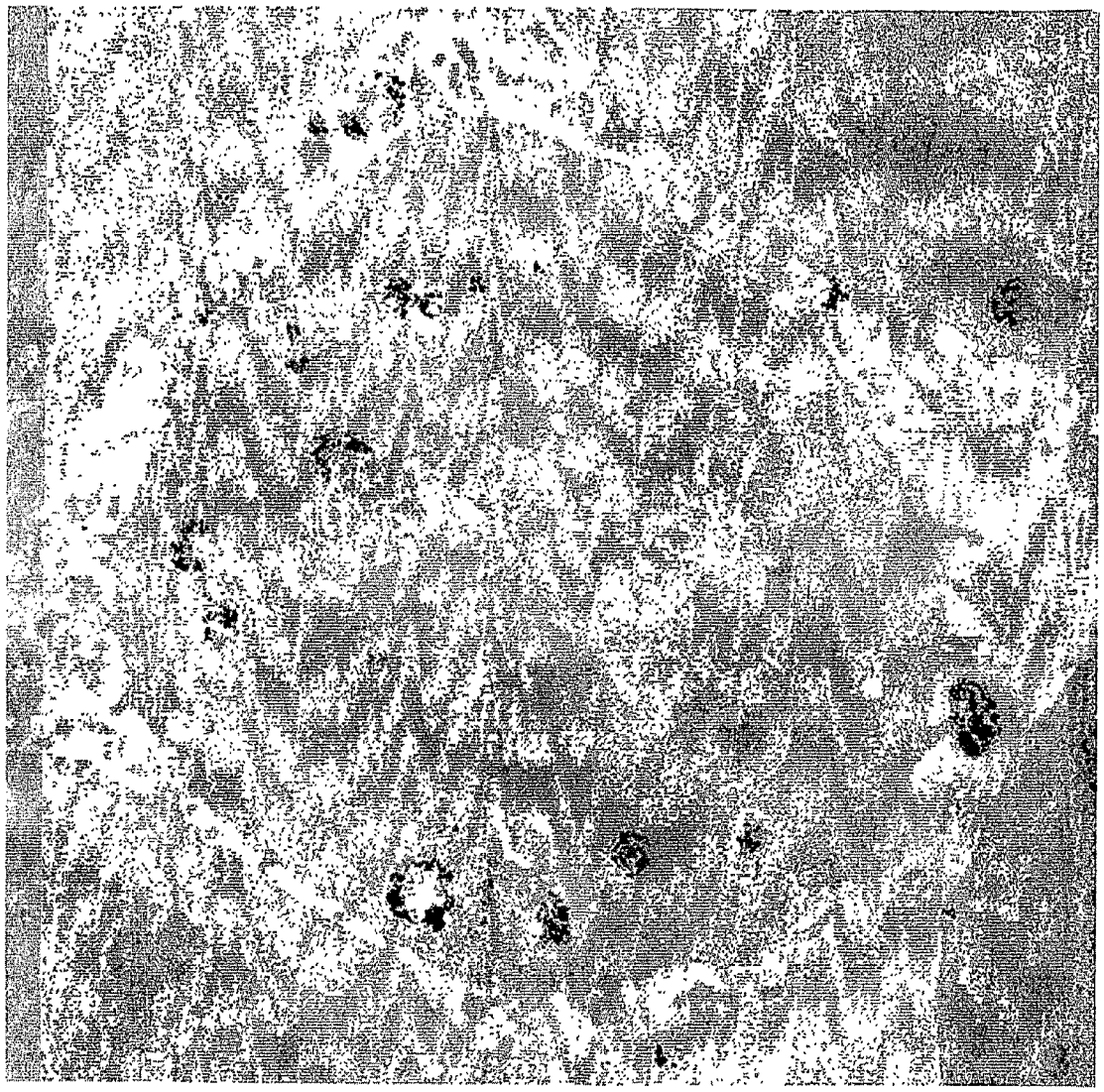
FIG. 14. Cryo-EM images of C166 cells. Initial experiments indicate that ASODN-gold particles are concentrated into vesicles within the cytoplasm of the cell 48 hours post transfection.

Twenty four hours post transfection with 0.024 nmol antisense nanoparticles, quantification with ICP-MS shows that 30% of these particles have entered C166 cells. By increasing the concentration to 0.048 nmol, the uptake is 40%. FIG. 14 shows Cryo-EM images of C166 cells, wherein initial experiments indicated that ASODN-gold particles were concentrated in vesicles within the cytoplasm of the cell 48 hours post transfection. While these results will vary between cell types, it provides evidence that the particles can quickly enter cells and therefore may be less susceptible to degradation factors. It also demonstrates that the quantity of particles, and therefore number of oligonucleotides delivered to the cells can be precisely determined.

In other uptake experiments, C. elegans were incubated with 0.048 nmol fluorophore-labeled antisense gold nanoparticles for 72 hours. Results showed fluorescence throughout the intestinal track with no observable toxicity.

Numerous modifications and variations in the invention as set forth in the above illustrative examples are expected to occur to those skilled in the art. Consequently only such limitations as appear in the appended claims should be placed on the invention.

What is claimed is:

1. A method of inhibiting expression of a gene product comprising the step of hybridizing a polynucleotide encoding said gene product with one or more oligonucleotides complementary to all or a portion of said polynucleotide, said oligonucleotide being covalently bound to an inorganic nanoparticle, wherein said nanoparticle does not comprise a targeting peptide, wherein hybridizing between said polynucleotide and said oligonucleotide, in a buffer and in the absence of a transfection reagent, occurs over a length of said polynucleotide with a degree of complementarity sufficient to inhibit expression of said gene product, wherein the expression is inhibited by at least 5% compared to expression in the absence of the oligonucleotide, and wherein said nanoparticle is not a dendrimer.

2. The method of claim 1 wherein expression of said gene product is inhibited in vitro or in vivo.

3. The method of claim 1 wherein said nanoparticle is metallic or is a colloidal metal, or is selected from the group consisting of a gold nanoparticle, a silver nanoparticle, a platinum nanoparticle, an aluminum nanoparticle, a palladium nanoparticle, a copper nanoparticle, a cobalt nanoparticle, an indium nanoparticle, and a nickel particle.

4. The method of claim 1 wherein said oligonucleotide is bound to said nanoparticle through one or more sulfur linkages.

5. The method of claim 1 wherein said oligonucleotide is about 5 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length.

6. The method of claim 1 wherein said oligonucleotide is a DNA oligonucleotide or an RNA oligonucleotide.

7. The method of claim 1 wherein said oligonucleotide is 100% complementary to said polynucleotide, greater than 95% complementary to said polynucleotide, greater than 90% complementary to said polynucleotide, greater than 80% complementary to said polynucleotide, greater than 75% complementary to said polynucleotide, greater than 70% complementary to said polynucleotide, greater than 65% complementary to said polynucleotide, greater than 60% complementary to said polynucleotide, greater than 55% complementary to said polynucleotide, or greater than 50% complementary to said polynucleotide.

8. The method of claim 1 wherein said oligonucleotide includes at least one modified internucleotide linkage selected from the group consisting of a peptide nucleic acid linkage, a phosphorothioate linkage, a morpholino linkage, a methylphosphonate linkage, or a sulfonyl linkage.

9. The method of claim 1 wherein said oligonucleotide includes at least one modified nucleic acid sugar moiety or at least one modified nucleic acid.

10. The method of claim 1 wherein said oligonucleotide is bound to said nanoparticle through a 5' linkage or a 3' linkage.

11. The method of claim 1 wherein said oligonucleotide comprises a tandem repeat of identical nucleotide sequences, and wherein said tandem repeat comprises two identical nucleotide sequences, three identical nucleotide sequences, four identical nucleotide sequences, five identical nucleotide sequences, or five or more identical nucleotide sequences.

12. The method of claim 11 wherein said identical nucleotide sequences in said tandem repeat are separated by a nucleotide spacer between each identical sequence.

13. The method of claim 1 wherein said oligonucleotide is bound through a spacer to said nanoparticle.

14. The method of claim 13 wherein said spacer is an organic moiety.

15. The method of claim 14 wherein said organic moiety is a polymer.

16. The method of claim 15 wherein said polymer is a water-soluble polymer, a nucleic acid, a polypeptide, or an oligosaccharide.

17. The method of claim 1 wherein said nanoparticle is bound to at least two oligonucleotides having different sequences.

18. The method of claim 17 wherein said different sequences hybridize to different regions on the same polynucleotide or to different polynucleotides.

19. The method of claim 1 wherein said polynucleotide is a mRNA encoding said gene product and translation of said gene product is inhibited.

20. The method of claim 1 wherein said polynucleotide is DNA in a gene encoding said gene product and transcription of said gene product is inhibited.

21. The method of claim 20 wherein said DNA encodes said gene product or is complementary to a sequence that encodes said gene product.

22. The method of claim 1 wherein said polynucleotide is a bacterial polynucleotide.

23. The method of claim 22 wherein said bacterial polynucleotide is bacterial genomic DNA or is RNA transcribed from bacterial genomic DNA.

24. The method of claim 1 wherein said polynucleotide is a viral polynucleotide.

25. The method of claim 24 wherein said viral polynucleotide is viral genomic RNA, viral genomic DNA, or RNA transcribed from viral genomic DNA.

26. The method of claim 1 wherein said polynucleotide is a fungal polynucleotide.

27. The method of claim 26 wherein said fungal polynucleotide is fungal genomic DNA or is RNA transcribed from fungal genomic DNA.

28. The method of claim 1 wherein expression of said gene product is inhibited by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%.

29. The method of claim 1 wherein said nanoparticle ranges from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, or about 1 nm to about 10 nm in mean diameter.

30. The method of claim 1 wherein said oligonucleotide is bound to said nanoparticle at a surface density of at least 10 pmol/cm$^2$, at least 15 pmol/cm$^2$, at least 20 pmol/cm$^2$, at least 10 pmol/cm$^2$, at least 25 pmol/cm$^2$, at least 30 pmol/cm$^2$, at least 35 pmol/cm$^2$, at least 40 pmol/cm$^2$, at least 45 pmol/cm$^2$, or at least 50 pmol/cm$^2$.

31. The method of claim 1 wherein expression of said gene product is associated with a disease state.

32. The method of claim 1 wherein said nanoparticle is optionally labeled.

33. The method of claim 1 wherein said nanoparticle further comprises a targeting molecule.

34. The method of claim 1 wherein said polynucleotide is a mitochondrial polynucleotide.

35. The method of claim 1 wherein packing density of the oligonucleotides on the surface of the nanoparticle is sufficient to result in cooperative behavior between said nanoparticles.

36. The method of claim 35 wherein the packing density of the oligonucleotides on the surface of the nanoparticle is greater than about 7000 oligonucleotides per square micron of nanoparticle surface.

37. The method of claim 35 wherein cooperative behavior between the nanoparticles increases the strength of the binding between the oligonucleotide and the polynucleotide, increases resistance of the oligonucleotide to degradation, increases resistance of the oligonucleotide-polynucleotide complex to degradation, or increases resistance of the oligonucleotide to degradation by a nuclease.

38. The method of claim 1 wherein said polynucleotide is an inhibitory RNA (RNAi) that performs a regulatory function.

39. The method of claim 38 wherein the RNAi is selected from the group consisting of a small inhibitory RNA (siRNA), an RNA that forms a triplex with double stranded DNA, and a ribozyme.

40. The method of claim 1 wherein the oligonucleotide is complementary to a regulatory region of the polynucleotide.

41. The method of claim 1 wherein the oligonucleotide is released from the nanoparticle after the nanoparticle enters a cell.

42. A method of inhibiting expression of a gene product comprising the step of hybridizing a polynucleotide encoding said gene product with one or more oligonucleotides complementary to all or a portion of said polynucleotide, said oligonucleotide being covalently bound to a nanoparticle, wherein said nanoparticle does not comprise a targeting peptide, wherein hybridizing between said polynucleotide and said oligonucleotide, in a buffer and in the absence of a transfection reagent, occurs over a length of said polynucleotide with a degree of complementarity sufficient to inhibit expression of said gene product, wherein the expression is inhibited by at least 5% compared to expression in the absence of the oligonucleotide, and wherein said nanoparticle is not a dendrimer or polyethylene.

* * * * *